United States Patent

Wingert et al.

[11] Patent Number: 5,506,263
[45] Date of Patent: Apr. 9, 1996

[54] BENZYL DERIVATIVES AND PESTICIDES CONTAINING THEM

[75] Inventors: Horst Wingert; Hubert Sauter, both of Mannheim; Eberhard Ammermann, Heppenheim; Gisela Lorenz, Neustadt, all of Germany

[73] Assignee: BASF Aktiengesellschaft, Ludwigshafen, Germany

[21] Appl. No.: 355,545

[22] Filed: Dec. 14, 1994

Related U.S. Application Data

[63] Continuation of Ser. No. 99,692, Jul. 30, 1993, Pat. No. 5,416,110.

[30] Foreign Application Priority Data

Aug. 8, 1992 [DE] Germany ............... 42 26 303.4

[51] Int. Cl.$^6$ ............... A01N 47/10; C07C 333/04; C07C 271/08
[52] U.S. Cl. ............... 514/488; 514/256; 514/275; 514/352; 514/371; 514/383; 514/398; 514/426; 514/447; 514/472; 514/322; 514/326; 514/330; 514/332; 546/305; 548/196; 548/265.4; 548/326.5; 548/557; 548/558; 548/331.1; 548/341.5; 549/69; 549/480; 558/235; 558/270; 558/271; 558/272; 558/273; 558/275; 558/276; 560/31
[58] Field of Search ............... 514/488, 256, 514/275, 352, 371, 383, 348, 426, 447, 472; 549/69, 480; 548/196, 265.4, 305, 326.5, 557, 558; 546/305; 544/322, 326, 330, 332; 558/235, 270, 271, 272, 273, 275, 276; 560/31

[56] References Cited

PUBLICATIONS

CA 113: 190939k Preparation of . . . fungicides. Richards et al., p. 680, 1990.
CA 114: 81863f Preparation of . . . fungicides. Cliff et al., p. 741–742, 1991.
CA 119: 203175j Derivatives of . . . fungicides. Matthews et al., p. 867, 1993.

*Primary Examiner*—Joseph K. McKane
*Attorney, Agent, or Firm*—Oblon, Spivak, McClelland, Maier & Neustadt

[57] ABSTRACT

Benzyl derivatives of the formula I

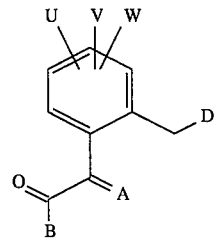

where
A is $CH_2$, CHCl, CH-alkyl, CH-alkoxy, CH-alkylthio or N-alkoxy,
B is OH, alkylthio, alkoxy or alkylamino,
U, V, W are hydrogen, halogen, alkyl or alkoxy,
D is

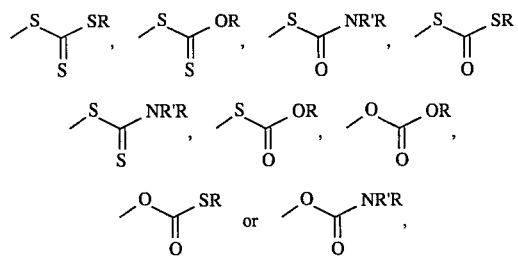

where
R' is hydrogen or alkyl and
R is hydrogen, alkyl, cycloalkyl, haloalkyl, halocycloalkyl, cycloalkylalkyl, alkoxyalkyl, alkylthioalkyl, arylthioalkyl, aryloxyalkyl, aryl, arylalkyl, hetaryl, hetaryl-alkyl, hetaryloxyalkyl or heterocyclyl, and fungicides containing these compounds.

13 Claims, No Drawings

BENZYL DERIVATIVES AND PESTICIDES CONTAINING THEM

This is a Continuation of application Ser. No. 08/099,692 filed on Jul. 30. 1993, now U.S. Pat. No. 5,416,110.

The present invention relates to novel benzyl derivatives and pesticides for controlling pests, in particular fungi, insects, nematodes and spider mites. It is known that certain β-methoxyacrylates (cf. European Patent 178,826) as well as certain oxime ethers (cf. European Patent 253,213) have fungicidal or insecticidal activity. However, their action is unsatisfactory.

We have found, surprisingly, that benzyl derivatives of the general formula I

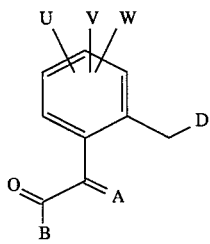

where
A is $CH_2$, CHCl, CH—$C_1$–$C_4$-alkyl, CH—$C_1$–$C_4$-alkoxy, CH—$C_1C_4$-alkylthio or N—$C_1$–$C_4$-alkoxy,
B is OH, $C_1$–$C_4$-alkylthio, $C_1$–$C_4$-alkoxy or $C_1$–$C_4$-alkylamino,
U, V and W are identical or different and are each hydrogen, halogen, $C_1$–$C_4$-alkyl or $C_1$–$C_4$-alkoxy,
D is

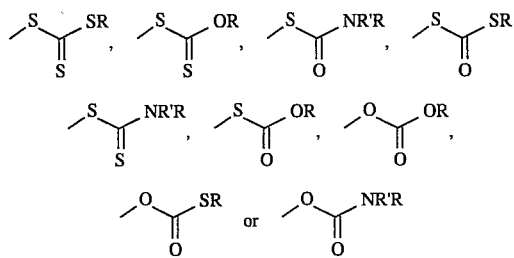

where
R' is hydrogen or $C_1$–$C_4$-alkyl,
R is hydrogen, $C_1$–$C_{10}$-alkyl, $C_3$–$C_6$-cycloalkyl, $C_1$–$C_4$-haloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, unsubstituted or substituted arylthio-$C_1$–$C_4$-alkyl, unsubstituted or substituted aryloxy-$C_1$–$C_4$-alkyl, unsubstituted or substituted aryl, unsubstituted or substituted aryl-$C_1$–$C_4$-alkyl, unsubstituted or substituted hetaryl, unsubstituted or substituted hetaryl-$C_1$–$C_4$-alkyl, unsubstituted or substituted hetaryloxy-$C_1$–$C_4$-alkyl or unsubstituted or substituted heterocyclyl, substituents being halogen, cyano, $CO_2(C_1$–$C_4$-alkyl), $CO(C_1$–$C_4$-alkyl), nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy, have an excellent fungicidal, insecticidal, nematicidal and acaricidal action which is better than that of the known β-methoxyacrylates or oxime ethers. The fungicidal action is preferred.

The radicals stated for the general formula I may have, for example, the following meanings:

A may be $C_1$–$C_4$-alkylidene (eg. methylidene, ethylidene, n-propylidene, isopropylidene, n-butylidene, isobutylidene, sec-butylidene or tert-butylidene), $C_1$–$C_4$-alkoxymethylidene (eg. methoxy-, ethoxy-, n-propoxy-, isopropoxy-, n-butoxy-, isobutoxy-, sec-butoxy- or tert-butoxymethylidene), $C_1$–$C_4$-alkylthiomethylidene (eg. methyl-, ethyl-, n-propyl-, isopropyl-, n-butyl-, isobutyl-, sec-butyl- or tert-butyl-thiomethylidene), $C_1$–$C_4$-alkoximino (eg. methoximino, ethoximino, n-propoximino, isopropoximino, n-butoximino, isobutoximino, sec-butoximino or tert-butoximino or chloromethylidene, B may be OH, $C_1$–$C_4$-alkoxy (eg. methoxy, ethoxy, n-propoxy, isopropoxy, n-butoxy, isobutoxy, sec-butoxy or tert-butoxy), $C_1$–$C_4$-alkylthio (eg. methylthio, ethylthio, n-propylthio, isopropylthio, n-butylthio, isobutylthio, sec-butylthio or tert-butylthio) and $C_1$–$C_4$-alkylamino (eg. methylamino, ethylamino, n-propylamino, isopropylamino, n-butylamino, isobutylamino, sec-butylamino or tert-butylamino), U, V and W may each be H, halogen (eg. fluorine, chlorine, bromine or iodine), methyl or methoxy, D may be

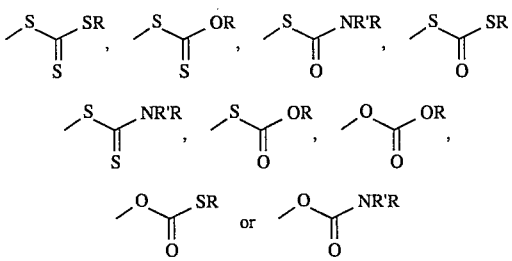

R' may be hydrogen or $C_1$–$C_4$-alkyl (eg. methyl, ethyl, n-propyl, isopropyl, n-butyl, isobutyl, sec-butyl or tert-butyl) and R may be straight-chain or branched $C_1$–$C_{10}$-alkyl (eg. methyl, ethyl, n-propyl, isopropyl, n-butyl, isobutyl, sec-butyl, tert-butyl, n-pentyl, isopentyl, sec-pentyl, tert-pentyl, neopentyl, n-hexyl or n-decyl), $C_3$–$C_6$-cycloalkyl (eg. cyclopropyl, cyclobutyl, cyclopentyl or cyclohexyl), $C_1$–$C_4$-haloalkyl (eg. trifluoromethyl, 2-fluoroethyl, 2,2,2-trifluoroethyl, pentafluoroethyl, fluorodichloromethyl, difluorochloromethyl, chloromethyl, trichloromethyl, 2-chloroethyl, 2,2,2-trichloroethyl or pentachloroethyl), $C_3$–$C_6$-halocycloalkyl (eg. 2,2-difluorocyclopropyl, 2,2-dichlorocyclopropyl, 2,2-dibromocyclopropyl, 2,2-dichloro- 3-methylcyclopropyl or tetrafluorocyclobutyl), $C_3$–$C_6$-cycloalkyl-$C_1$–$C_4$-allyl (eg. 1-methylcyclopropyl, 2,2-dimethylcyclopropyl or 1-methylcyclohexyl), $C_1$–$C_4$-alkoxy-$C_1$–$C_4$-alkyl (eg. methoxymethyl, ethoxymethyl, n-propoxylmethyl, isopropoxylmethyl, n-butoxymethyl, isobutoxymethyl, sec-butoxymethyl, tert-butoxymethyl, 2-methoxyprop- 2-yl, 2-ethoxyprop-2-yl, 2-n- or isopropoxyprop- 2-yl, 2-n-, iso-, sec- or tert-butoxyprop-2-yl), $C_1$–$C_4$-alkylthio-$C_1$–$C_4$-alkyl (eg. methylthiomethyl, ethylthiomethyl, n-propylthiomethyl, isopropylthiomethyl, n-butylthiomethyl, isobutylthiomethyl, sec-butylthiomethyl, tert-butylthiomethyl, 2-methylthioprop-2-yl,2-ethylthioprop-2-yl, 2-n- or isopropylthioprop-2-yl, 2-n-, iso-, sec- or tert-butylthioprop-2-yl), aryl(phenyl)thio-$C_1$–$C_4$-alkyl (eg. phenylthiomethyl or 2-chlorophenylthiomethyl), unsubstituted or substituted aryloxy-$C_1$–$C_4$-alkyl (eg. phenoxymethyl), unsubstituted or substituted aryl (eg. phenyl, naphthyl or anthryl), unsubstituted or substituted aryl-$C_1$–$C_4$-alkyl (eg. benzyl, 1-phenethyl, 2-phenethyl, 1-phenylpropyl, 2-phenylpropyl, 3-phenylpropyl, 2-methyl-3-phenylpropyl, 2-methyl-2-phenylpropyl or 4-phenylbutyl), unsubstituted or substituted hetaryl (eg. pyridyl, 2-pyridyl, 3-pyridyl, 4-pyridyl, pyrimidinyl, 4-pyrimidinyl, 2-pyrimidinyl, thienyl, 2-thienyl, 3-thienyl, furyl, 2-furyl, 3-furyl, 1-pyrrolyl, 1-imidazolyl, 1,2,4-triazolyl, 1,3,4-triazolyl, 4-thiazolyl or 2-benzothiazolyl), unsubstituted or substituted hetaryl-$C_1$–$C_4$-alkyl (eg. 2-pyridylmethyl or 3-pyridylmethyl), unsubstituted or substituted hetaryloxy-$C_1$–$C_4$-alkyl (eg. furfurylmethoxy) or unsubstituted or substituted heterocyclyl (eg. oxiranyl, 1-aziridinyl, 1-azetidinyl, 1-pyrrolidinyl, 2-tetrahydrofuryl, 2-tetrahydropyranyl, 3-tetrahydropyranyl, 1-piperidinyl, 1-morpholinyl, 1-piperazinyl, 1,3-dioxanyl or 3-tetrahydrothiopyranyl).

The radicals referred to as being unsubstituted or substituted above are substituted, apart from hydrogen, for example by fluorine, chlorine, bromine, iodine, cyano, nitro, methyl, ethyl, isopropyl, tert-butyl, methoxy, ethoxy, isopropoxy, tert-butoxy, trifluoromethyl, chloromethyl, dichloromethyl, trichloromethyl, trifluoromethoxy, 1,1,2,2-tetrafluoroethoxy, methoximinomethyl, ethoximinomethyl, n-propoximinomethyl, n-butoximinomethyl n-pentyloximinomethyl, n-hexyloximinomethyl, allyloximinomethyl, benzyloximinomethyl, isopropoximinomethyl, isobutoximinomethyl, tert-butoximinomethyl, methylimino-1-ethyl, ethoximino-1-ethyl, n-propoximino-1-ethyl, n-butoximino-1-ethyl, n-pentyloximino-1-ethyl, n-hexyloximino-1-ethyl, allyloximino-1-ethyl, benzyloximino-1-ethyl, phenyl, phenoxy, benzyloxy, imidazol-1-yl, piperazin-1-yl, 4-morpholinyl, piperidin-1-yl, pyrid-2-yloxy, cyclopropyl, cyclohexyl, oxiranyl, 1,3-dioxan-2-yl, 1,3-dioxolan-2-yl or tetrahydropyran-2-yloxy.

Preferred compounds of the general formula I are those in which

A is $CHCH_3$, $CHCH_2CH_3$, $CHOCH_3$ or $NOCH_3$,
B is $OCH_3$ or $NHCH_3$,
U, V and W are each hydrogen,
R' is hydrogen and methyl or
D and R each have the meanings stated in claim 1.

Owing to the C=C or C=N double bonds, the novel compounds of the general formula I may be obtained in the preparation as E/Z isomer mixtures. These can be separated into the individual components in a conventional manner, for example by crystallization or chromatography. Both the individual isomeric compounds and mixtures thereof form subjects of the invention and can be used as pesticides.

The preparation of the compounds of the general formula I as claimed in claim I is carried out, for example, as described in Scheme 1.

Scheme 1

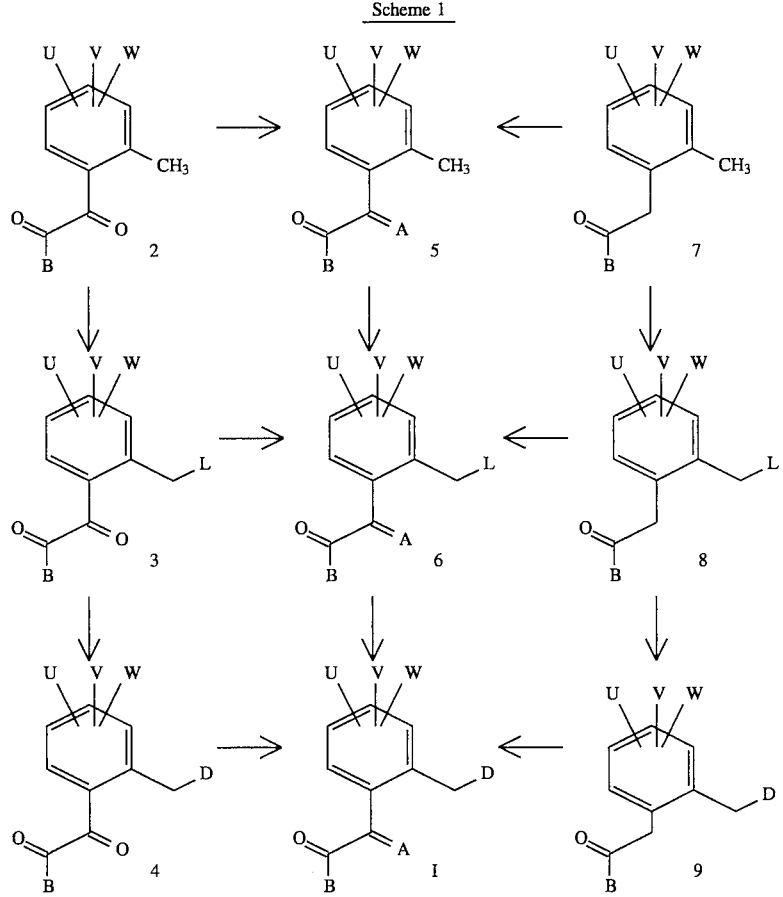

The compounds of the general formula I where A is $CH_2$, CH-Alkyl or CH-Alkoxy can be prepared, for example, from the ketoester 4 by a Wittig or Wittig-Horner reaction (cf. European Patents 348,766 or 178,826 or German Patent 3,705,389). The similar compounds 5 are obtained from the ketoesters 2 in the same manner.

In an alternative procedure, a compound of the formula 7 or 9 is condensed with a suitable reagent, for example with formaldehyde where A is CH$_2$ (cf. German Patent 3,317, 356), a) with an aldehyde (cf. D. M. Brown, J. Chem. Soc. (1948), 2147) or b) first with N,N-dimethylformamide dimethyl acetal followed by reaction with a Grignard reagent where A is CH-Alkyl (similarly to C. Jutz, Chem. Ber. 91 (1958), 1867), with a formate followed by alkylation where A is CH-O-Alkyl (cf. European Patent 178,826). Further preparation methods for the compounds of the formula 5 and I where A is CH-O-Alkyl are described in European Patent 178,826.

A further possibility for the preparation of the compounds of the formula I where A is CH-Alkyl and B is O-Alkyl is the reaction of ketene acetals with phenyl chlorocarbonates (cf. N. Slougui, G. Rousseau, Synth. Commun. 12 (5) (1982), 401–407).

For compounds of the general formula I where A is CH-S-Alkyl and A is CHCl, the preparation can be carried out by the methods from European Patent 244,077 or 310,954.

The intermediates of the formulae 3, 6 and 8 can be prepared from the compounds 2, 5 and 7 by halogenating the latter by known methods, for example with chlorine, bromine or N-bromosuccinimide in an inert solvent (eg. CCl$_4$ or cyclohexane) with exposure to, for example, an vapor lamp or using a free radical initiator, such as dibenzoyl peroxide, or by introducing the radicals L, such as mesylate, rosylate, acetate or triflate, via suitable intermediates (L is halogen or The oxime ethers of the formula I where A is N-O-Alkyl can be prepared from 4 a) by reaction with an O-Alkylhydroxylamine hydrochloride or b) with hydroxylamine hydrochloride and subsequent alkylation with an alkylating agent (eg. an alkyl iodide, dialkyl sulfate, etc.) (cf. German Patent 3,623,921).

Using the methods similar to that in European Patent 254,426, a phenylacetate of the formula 9 can be converted with a base (eg. NaOMe, NaH, K tert-butylate, etc.) in a solvent (such as diethyl ether, toluene, tert-butanol, etc.) into its anion and can be oximated with a suitable nitrosating agent (such as methyl nitrite, amyl nitrite, tert-butyl nitrite, etc.). The resulting oximate is alkylated with an alkylating agent (eg. an alkyl iodide or dialkyl sulfate).

The same methods can also be applied to the compounds of the formulae 2 and 7, and the resulting oxime ethers 5 can be converted in a known manner (European Patent 254,426) via the intermediates 6 (L is, for example, halogen) into the desired compounds I.

The novel compounds of the general formula I are obtained specifically by reacting a benzyl derivative having a suitable leaving group L (eg. halogen) 6 with a carbonic acid salt 10 in an inert solvent or diluent.

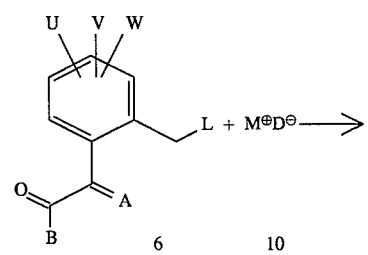

Specifically, the novel compounds are obtained as follows:

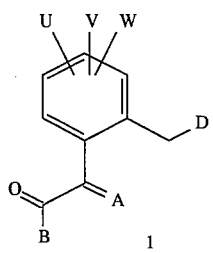

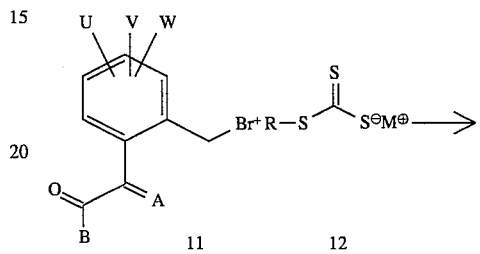

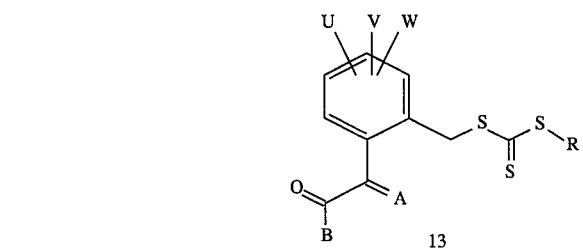

Trithiocarbonates 13 are obtained, for example, by reacting the metal salts 12 with the benzyl bromides 11 by methods similar to known ones (cf. for example Houben-Weyl, Vol. E 4, page 451 et seq. (1983)).

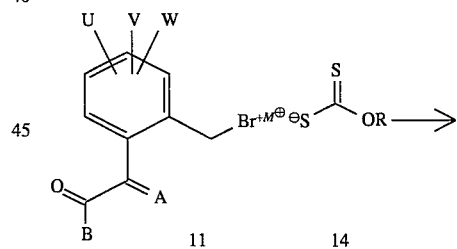

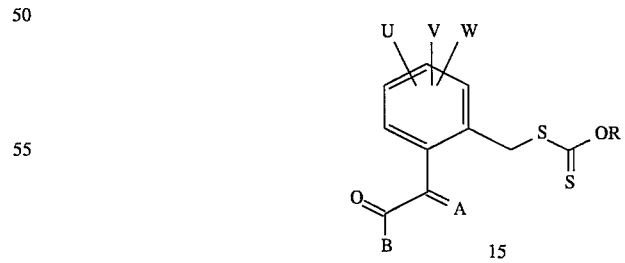

The dithiocarbonates 15 can be prepared, for example, by reacting the benzyl bromides 11 with the metal salts 14 by methods similar to known ones (cf. for example R. Degani, Synthesis, (1975), 365).

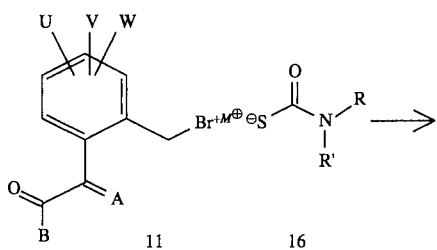

Dithiocarbamates of the type 17 are obtained, for example, in the reaction with the benzyl bromides 11 with the compounds 16 by methods similar to known ones (cf. for example Houben-Weyl, Vol. E 4, page 299 et seq. (1983)).

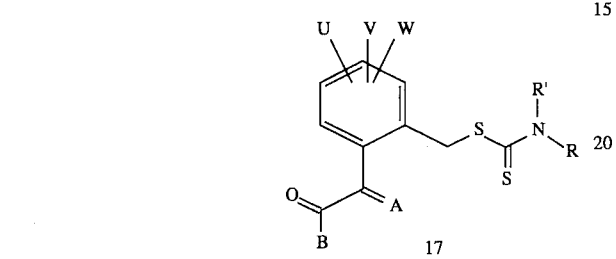

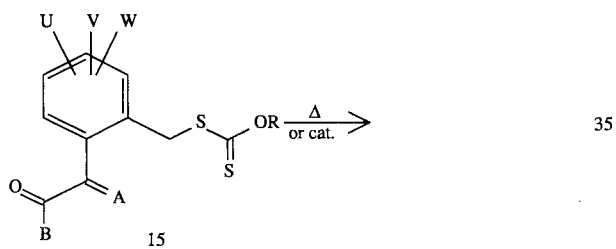

The dithiocarbonic acid derivatives 18 may be obtained by thermal or acid-catalyzed rearrangement from the dithiocarbonic acid derivatives 15 (cf. for example Houben-Weyl, Vol. E 4, page 133 et seq. (1983)).

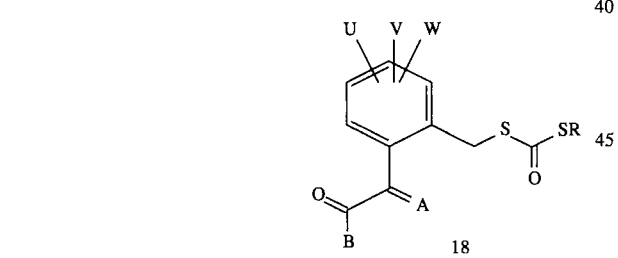

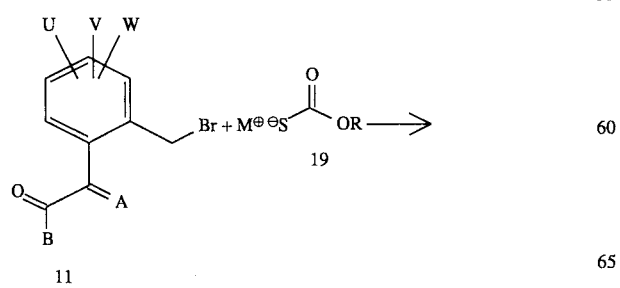

-continued

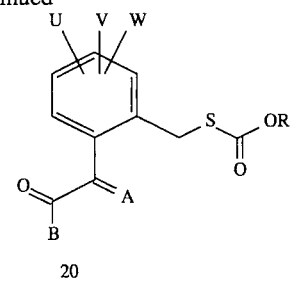

The thiocarbonates 20 are prepared, for example, by reaction of the benzyl bromides 11 with thiocarbonates 19 analogously to known processes (cf. for example Houben-Weyl Vol. E 4, page 108 et seq. (1983)).

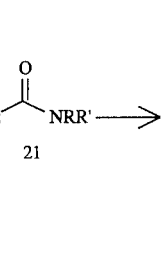

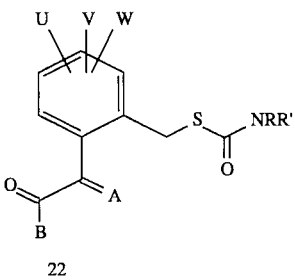

Thiocarbamic acids 22 are accessible by reaction of the benzyl bromides 11 with metal salts 21 analogously to known processes (cf. for example Houben-Weyl, Vol. E 4, page 299 (1983)).

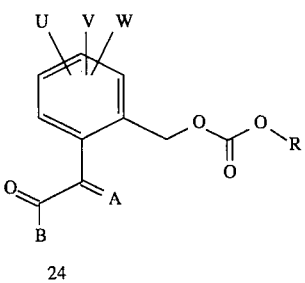

Carbonic diesters 24 are obtained by methods similar to known ones, by reacting the benzyl bromides 11 with carbonates 23 (cf. for example V. F. Pozdner, Zh. Org. Khim. 12 (1976), 1407).

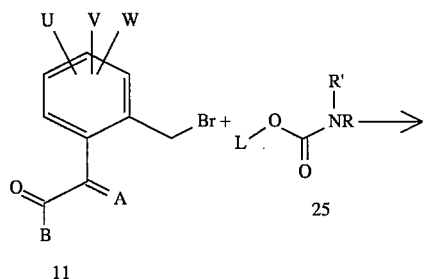

The carbamates 26 are obtainable by methods similar to known ones, from the benzylbromides 11 and the phosphacarbamates 25 (cf. for example M. Aresta, JOC 53 (1988), 4153).

The carboxylic acid metal salts 12, 14, 16, 19, 21, 23 and 25 are known or can be prepared by methods known from the literature (cf. Houben-Weyl, Vol. E 4).

In the preparation processes described above, B is usually alkoxy and U, V and W are each usually H.

The compounds in which B is OH (28) can be prepared by methods known from the literature (Organikum 16th Edition, pages 415 and 622), from the compounds of the general formula I where B is O-Alkyl (27) (cf. Scheme 2):

The acyl chlorides 29 can be prepared from the resulting carboxylic acids 28 in a conventional manner (cf. Organikum 16th Edition, page 423 et seq. (1985)). The conversion of 29 into the amides 30 is carried out similarly to Organikum 16th Edition, page 412 (1985).

The thioesters 31 are obtained from the acyl chlorides 29 (similarly to Houben-Weyl, Vol. 8, page 464 et seq. (1952)).

Alternatively, the thioesters 31 can also be obtained from the acids 28 (similarly to Houben-Weyl, Vol. E5, page 855 et seq. (1985)).

The amides 30 can also be prepared from the esters 27 by methods known from the literature.

The preparation of the compounds of the general formulae 2 and 7 which are ortho-substituted by methyl on the aromatic moiety is known (B is O-Alkyl and U, V and W are each H; cf. European Patents 178,826 and 260,832).

The reactions described can be carried out, for example, in an inert solvent or diluent (eg. acetone, acetonitrile, dimethylformamide, dimethyl sulfoxide or N-methylpyrrolidone) using a base (eg. sodium carbonate, potassium carbonate, sodium hydroxide, potassium hydroxide, sodium hydride or sodium methylate).

The reaction can also be carried out in a two-phase system (eg. dichloromethane, water) with the addition of a suitable phase transfer catalyst (eg. cetyltrimethylammoniumchloride or benzyltriethylammonium chloride).

EXAMPLES

EXAMPLE 1

Methyl 2-methoximino-2-{2-[(methyl-4-methylphenylthiocarbamoylsulfonyl)-methyl]-phenyl}-acetate (compound No. 157 in Table 2)

A pinch of potassium iodide is added to a solution of 3.6 g (17.5 mmol) of sodium N-methyl-N-4-methylphenyldithiocarbamate and 5 g (17.5 mmol) of methyl 2-methoximino- 2-(2'-bromomethyl)-phenylacetate in 50 ml of Scheme 2:

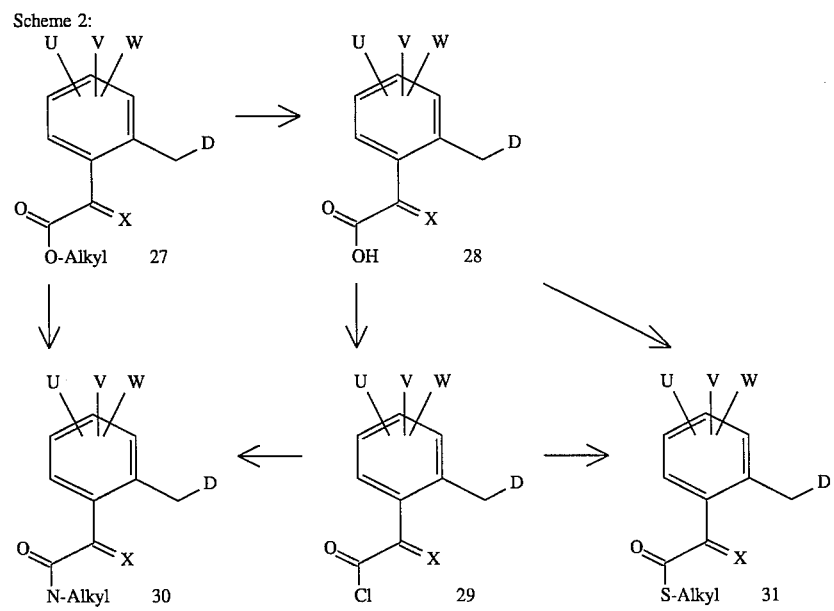

acetone and stirring is carried out for 15 hours at room temperature. Thereafter, the mixture is filtered under suction and the mother liquor is evaporated down. The residue is stirred in ether and filtered off under suction. 4.6 g (65%) of compound No. 157 (Table 2) remain as a colorless solid.

m.p.: 109°–113° C.

$^1$H-NMR (CDCl$_3$/TMS): δ=2.35; 3.72; 3.77; 3.97 (each s, 3H, CH$_3$); 4.30 (hr, 2H, CH$_2$); 7.07–7.47 ppm (m, 8H, aryl-H).

EXAMPLE 2

Preparation of compound 157, Table 4

1 g (2.5 mmol) of the compound prepared in Example 1 is heated with 50 ml of 40% strength N-methylamine solution for 2 hours at 40° C. Extraction is then carried out three times with ether, and the combined organic phases are dried and evaporated down. 1 g of the N-methylamide compound (No. 157, Table 4) remains as a colorless solid.

$^1$H-NMR (CDCl$_3$/TMS): δ=2.35; 3.72; 3.88 (each s, 3H, CH$_3$); 2.89 (d, 3H, NHCH$_3$); 4.32, (s, 2H, CH$_2$); 6.67 (br, 1H, NH); 7.05–7.43 ppm (m, 8H, aryl-H).

EXAMPLE 3

Preparation of compound No. 157, Table 1

A pinch of potassium iodide is added to a solution of 1.4 g (7 mmol) of sodium N-methyl-N-4-methylphenyldithiocarbamate and 2 g (7 mmol) of methyl α-(2-bromomethylphenyl)-β-methoxyacrylate in 50 ml of acetone and stirring is carried out for 16 hours at room temperature. Thereafter, the mixture is filtered under suction and the mother liquor is evaporated down. The remaining residue is chromatographed over silica gel using hexane/methyl tert-butyl ether. 1.2 g (43%) of compound No. 157 (Table 1) are obtained as a colorless solid.

mp.: 98°–99° C.

$^1$H-NMR (CDCl$_3$/TMS): δ=2.33; 3.57; 3.74 (each s, 3H, CH$_3$); 4.35 (s, 2H, CH$_2$); 7.05–7.43 (m, 8H, aryl-H); 7.51 (s, 1H, =CH).

EXAMPLE 4

Preparation of 2-hydroxymethyl-α-methoxyiminophenylacetic acid monomethylamide

A mixture of 57 g (200 mmol) of methyl 2-methoximino-2-(2-bromomethyl)phenylacetate, 29 g (300 mmol) of potassium acetate and a spatula tip of potassium iodide is heated in 300 ml of dimethylformamide for 30 minutes at 90° C. After the mixture has cooled it is stirred into ice water. The precipitate is filtered with suction, washed with water and dried; colorless crystals, mp. 70°–72° C., yield 50 g (94% of theory).

The compound thus obtained (50 g/188 mmol) is dissolved in 500 ml of THF, 100 ml (1.12 mol) of 40% strength aqueous methylamine solution are added and the mixture is stirred for 22 hours at room temperature. The mixture is evaporated down, and the residue is taken up in ethyl acetate, washed twice with saturated sodium chloride solution, dried over magnesium sulfate and evaporated down. The oily residue gradually solidifies on standing; the product crystallizes on trituration with diisopropyl ether/ligroin. Beige-colored crystals, mp. 99°–103° C., yield 32 g (82% of theory).

$^1$H-NMR (CDCl$_3$/δ scale): 2.90 (d, 3H, NCH$_3$); 3.48 (br t, 1H, OH); 2, 3H, OCH$_3$); 4.40 (d, 2H, CH$_2$O); 7.05 (br, 1H, NH); 7.14 (dd, 1H) and 7.2–7.6 (m, 3H, aromatic protons)

IR (KBr, ~ in cm$^{-1}$): 3384, 3306, 3281, 1647, 1035

EXAMPLE 5

Preparation of 2-(4-fluoroanilinocarbonyloxymethyl)-α-methoxyiminophenylacetic acid monomethylamide (Comp. 293, Tab. 4)

a) 2.2 g (10 mmol) of the compound obtained in Example 4, 1.4 g (10 mmol) of 4-fluorophenyl isocyanate and a spatula tip of 4-N,N-dimethylaminopyridine are stirred in 150 ml of toluene for 4 hours at 100° C. The product precipitates out on cooling. It is filtered with suction, washed with toluene and dried. Colorless crystals, mp. 208°–209° C., yield 2.4 g (67% of theory). The compound is a 3:1 mixture of two rotamers.

$^1$H-NMR (CDCl$_3$/δ scale): 2.81 and 2.90 (2d, tog. 3H, NCH$_3$ in both rotamers); 3.96 and 4.01 (2s, tog. 3H, OCH$_3$); 5.08 and 5.36 (2s, tog. 2H, OCH$_2$); 6.7–7.5 (several multiplets, tog. 10H, aromatic protons and both NH).

b) 2.2 g (10 mmol) of the compound obtained in Example 4 were suspended in 200 ml of toluene and heated to 60° C.; first 1.74 g (10 mmol) of 4-fluorophenyl chloroformate and then 1.5 ml (1.1 g/10 mmol) of triethylamine were added dropwise. The mixture was stirred for 2 hours and allowed to cool, the precipitate was filtered with suction, the filtrate was washed several times with water, dried over magnesium sulfate and evaporated down. 3.0 g (83% of theory) of the compound (No. 293; Tab. 4) were obtained.

The compounds shown in the Tables below are prepared according to the Examples described.

TABLE 1

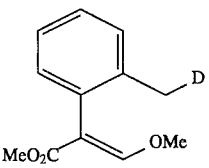

| No. | D | R' | R | phys. data$^{a)}$ |
|---|---|---|---|---|
| 1 | SC(S)NR'R | CH$_3$ | methyl | |
| 2 | SC(S)NR'R | CH$_3$ | ethyl | |
| 3 | SC(S)NR'R | CH$_3$ | n-propyl | |

TABLE 1-continued

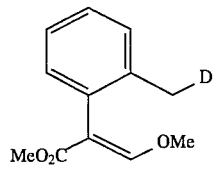

| No. | D | R' | R | phys. data[a] |
|---|---|---|---|---|
| 4 | SC(S)NR'R | CH₃ | tert.-butyl | |
| 5 | SC(S)NR'R | CH₃ | cyclopropyl | |
| 6 | SC(S)NR'R | CH₃ | cyclohexyl | 3.70, 3.85(3H), 4.50(2H), 7.63(1H) |
| 7 | SC(S)NR'R | CH₃ | methoxymethyl | |
| 8 | SC(S)NR'R | CH₃ | phenoxymethyl | |
| 9 | SC(S)NR'R | CH₃ | methylthiomethyl | |
| 10 | SC(S)NR'R | CH₃ | phenyl | 3.55; 3.71; 3.76(3 × 3H); 4.37(2H); 7.03–7.40(9H); 7.51(1H) |
| 11 | SC(S)NR'R | CH₃ | 2-fluorophenyl | |
| 12 | SC(S)NR'R | CH₃ | 3-fluorophenyl | 102–106° C. |
| 13 | SC(S)NR'R | CH₃ | 4-fluorophenyl | 3.57; 3.73; 3.74(3 × 3H); 4.35(2H); 7.04–7.43(8H), 7.51(1H) |
| 14 | SC(S)NR'R | CH₃ | pentafluorophenyl | |
| 15 | SC(S)NR'R | CH₃ | 2-chlorophenyl | |
| 16 | SC(S)NR'R | CH₃ | 3-chlorophenyl | 3.57; 3.72; 3.74(3 × 3H); 4.34(2H); 7.04–7.43(8H), 7.51(1H) |
| 17 | SC(S)NR'R | CH₃ | 4-chlorophenyl | 3.00, 3.71, 3.86(3H), 4.35(2H) |
| 18 | SC(S)NR'R | CH₃ | pentachlorophenyl | |
| 19 | SC(S)NR'R | CH₃ | 2,3-dichlorophenyl | |
| 20 | SC(S)NR'R | CH₃ | 2,4-dichlorophenyl | |
| 21 | SC(S)NR'R | CH₃ | 2,5-dichlorophenyl | |
| 22 | SC(S)NR'R | CH₃ | 2,6-dichlorophenyl | |
| 23 | SC(S)NR'R | CH₃ | 3,4-dichlorophenyl | |
| 24 | SC(S)NR'R | CH₃ | 3,5-dichlorophenyl | |
| 25 | SC(S)NR'R | CH₃ | 2,3,4-trichlorophenyl | |
| 26 | SC(S)NR'R | CH₃ | 2,3,5-trichlorophenyl | |
| 27 | SC(S)NR'R | CH₃ | 2,3,6-trichlorophenyl | |
| 28 | SC(S)NR'R | CH₃ | 2,4,5-trichlorophenyl | |
| 29 | SC(S)NR'R | CH₃ | 2,4,6-trichlorophenyl | |
| 30 | SC(S)NR'R | CH₃ | 3,4,5-trichlorophenyl | |
| 31 | SC(S)NR'R | CH₃ | 2,3,4,6-tetrachlorophenyl | |
| 32 | SC(S)NR'R | CH₃ | 2,3,5,6-tetrachlorophenyl | |
| 33 | SC(S)NR'R | CH₃ | 2-bromophenyl | |
| 34 | SC(S)NR'R | CH₃ | 3-bromophenyl | |
| 35 | SC(S)NR'R | CH₃ | 4-bromophenyl | |
| 36 | SC(S)NR'R | CH₃ | 2,4-dibromophenyl | |
| 37 | SC(S)NR'R | CH₃ | 3-bromo-4-fluorophenyl | |
| 38 | SC(S)NR'R | CH₃ | 3-bromo-4-methoxyphenyl | |
| 39 | SC(S)NR'R | CH₃ | 2-iodophenyl | |
| 40 | SC(S)NR'R | CH₃ | 3-iodophenyl | |
| 41 | SC(S)NR'R | CH₃ | 4-iodophenyl | |
| 42 | SC(S)NR'R | CH₃ | 2-chloro-4-fluorophenyl | |
| 43 | SC(S)NR'R | CH₃ | 2-chloro-5-fluorophenyl | |
| 44 | SC(S)NR'R | CH₃ | 2-chloro-6-fluorophenyl | |
| 45 | SC(S)NR'R | CH₃ | 2-chloro-4-bromophenyl | |
| 46 | SC(S)NR'R | CH₃ | 2-bromo-4-chlorophenyl | |
| 47 | SC(S)NR'R | CH₃ | 2-bromo-4-fluorophenyl | |
| 48 | SC(S)NR'R | CH₃ | 3-bromo-4-fluorophenyl | |
| 49 | SC(S)NR'R | CH₃ | 3-chloro-4-fluorophenyl | |
| 50 | SC(S)NR'R | CH₃ | 3-fluoro-4-chlorophenyl | |
| 51 | SC(S)NR'R | CH₃ | 2-cyanophenyl | |
| 52 | SC(S)NR'R | CH₃ | 3-cyanophenyl | |
| 53 | SC(S)NR'R | CH₃ | 4-cyanophenyl | |
| 54 | SC(S)NR'R | CH₃ | 2-nitrophenyl | |
| 55 | SC(S)NR'R | CH₃ | 3-nitrophenyl | |
| 56 | SC(S)NR'R | CH₃ | 4-nitrophenyl | |
| 57 | SC(S)NR'R | CH₃ | 2-methylphenyl | 2.17; 3.54; 3.69; 3.71; (4 × 3H); 4.35(2H); 7.03–7.41(8H); 7.51(1H) |
| 58 | SC(S)NR'R | CH₃ | 3-methylphenyl | 2.34; 3.65; 3.72; 3.74; (4 × 3H); 4.36(2H); 7.00–7.51(8H); 7.43(1H) |
| 59 | SC(S)NR'R | CH₃ | 4-methylphenyl | 98–99° C. |
| 60 | SC(S)NR'R | CH₃ | 2,4-dimethylphenyl | |
| 61 | SC(S)NR'R | CH₃ | 2,6-dimethylphenyl | 120–121° C. |
| 62 | SC(S)NR'R | CH₃ | 3,4-dimethylphenyl | |
| 63 | SC(S)NR'R | CH₃ | 3,5-dimethylphenyl | |
| 64 | SC(S)NR'R | CH₃ | 2,3,4-trimethylphenyl | |
| 65 | SC(S)NR'R | CH₃ | 2,3,5-trimethylphenyl | |
| 66 | SC(S)NR'R | CH₃ | 2,3,6-trimethylphenyl | |
| 67 | SC(S)NR'R | CH₃ | 2,4,5-trimethylphenyl | |

TABLE 1-continued

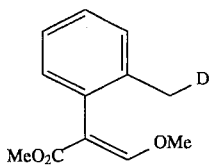

| No. | D | R' | R | phys. data[a)] |
|---|---|---|---|---|
| 68 | SC(S)NR'R | CH₃ | 2,4,6-trimethylphenyl | |
| 69 | SC(S)NR'R | CH₃ | 3,4,5-trimethylphenyl | |
| 70 | SC(S)NR'R | CH₃ | pentamethylphenyl | |
| 71 | SC(S)NR'R | CH₃ | 2-ethylphenyl | |
| 72 | SC(S)NR'R | CH₃ | 3-ethylphenyl | |
| 73 | SC(S)NR'R | CH₃ | 4-ethylphenyl | |
| 74 | SC(S)NR'R | CH₃ | 3,5-diethylphenyl | |
| 75 | SC(S)NR'R | CH₃ | 2-n-propylphenyl | |
| 76 | SC(S)NR'R | CH₃ | 3-n-propylphenyl | |
| 77 | SC(S)NR'R | CH₃ | 4-n-propylphenyl | |
| 78 | SC(S)NR'R | CH₃ | 2-isopropylphenyl | |
| 79 | SC(S)NR'R | CH₃ | 3-isopropylphenyl | |
| 80 | SC(S)NR'R | CH₃ | 4-isopropylphenyl | |
| 81 | SC(S)NR'R | CH₃ | 2,4-diisopropylphenyl | |
| 82 | SC(S)NR'R | CH₃ | 3,5-diisopropylphenyl | |
| 83 | SC(S)NR'R | CH₃ | 4-n-butyphenyl | |
| 84 | SC(S)NR'R | CH₃ | 4-sec.-butylphenyl | |
| 85 | SC(S)NR'R | CH₃ | 4-iso-butylphenyl | |
| 86 | SC(S)NR'R | CH₃ | 4-tert.-butylphenyl | |
| 87 | SC(S)NR'R | CH₃ | 3-tert.-butylphenyl | |
| 88 | SC(S)NR'R | CH₃ | 2-tert.-butylphenyl | |
| 89 | SC(S)NR'R | CH₃ | 2,4-di-tert.-butylphenyl | |
| 90 | SC(S)NR'R | CH₃ | 3,5-di-tert.-butylphenyl | |
| 91 | SC(S)NR'R | CH₃ | 4-n-hexylphenyl | |
| 92 | SC(S)NR'R | CH₃ | 4-n-dodecylphenyl | |
| 93 | SC(S)NR'R | CH₃ | 2-methyl-4-tert.-butylphenyl | |
| 94 | SC(S)NR'R | CH₃ | 2-methyl-6-tert.-butylphenyl | |
| 95 | SC(S)NR'R | CH₃ | 2-methyl-4-isopropylphenyl | |
| 96 | SC(S)NR'R | CH₃ | 2-methyl-4-cyclohexylphenyl | |
| 97 | SC(S)NR'R | CH₃ | 2-methyl-4-phenylphenyl | |
| 98 | SC(S)NR'R | CH₃ | 2-methyl-4-benzylphenyl | |
| 99 | SC(S)NR'R | CH₃ | 2-methyl-4-phenoxyphenyl | |
| 100 | SC(S)NR'R | CH₃ | 2-methyl-4-benzyloxyphenyl | |
| 101 | SC(S)NR'R | CH₃ | 2-methyl-3-chlorophenyl | |
| 102 | SC(S)NR'R | CH₃ | 2-methyl-4-chlorophenyl | |
| 103 | SC(S)NR'R | CH₃ | 2-methyl-5-chlorophenyl | |
| 104 | SC(S)NR'R | CH₃ | 2-methyl-6-chlorophenyl | |
| 105 | SC(S)NR'R | CH₃ | 2-methyl-4-fluorophenyl | |
| 106 | SC(S)NR'R | CH₃ | 2-methyl-3-bromophenyl | |
| 107 | SC(S)NR'R | CH₃ | 2-methyl-4-bromophenyl | |
| 108 | SC(S)NR'R | CH₃ | 2-methyl-3-methoxyphenyl | |
| 109 | SC(S)NR'R | CH₃ | 2-methyl-4-methoxyphenyl | |
| 110 | SC(S)NR'R | CH₃ | 2-methyl-5-methoxyphenyl | |
| 111 | SC(S)NR'R | CH₃ | 2-methyl-6-methoxyphenyl | |
| 112 | SC(S)NR'R | CH₃ | 2-methyl-4-isopropoxyphenyl | |
| 113 | SC(S)NR'R | CH₃ | 2-methyl-2,5-dimethoxyphenyl | |
| 114 | SC(S)NR'R | CH₃ | 2-methoxyphenyl | |
| 115 | SC(S)NR'R | CH₃ | 3-methoxyphenyl | |
| 116 | SC(S)NR'R | CH₃ | 4-methoxyphenyl | |
| 117 | SC(S)NR'R | CH₃ | 2,3-dimethoxyphenyl | |
| 118 | SC(S)NR'R | CH₃ | 2,4-dimethoxyphenyl | |
| 119 | SC(S)NR'R | CH₃ | 2,5-dimethoxyphenyl | |
| 120 | SC(S)NR'R | CH₃ | 2,6-dimethoxyphenyl | |
| 121 | SC(S)NR'R | CH₃ | 3,4-dimethoxyphenyl | |
| 122 | SC(S)NR'R | CH₃ | 3,5-dimethoxyphenyl | |
| 123 | SC(S)NR'R | CH₃ | 3,6-dimethoxyphenyl | |
| 124 | SC(S)NR'R | CH₃ | 2,3,4-trimethoxyphenyl | |
| 125 | SC(S)NR'R | CH₃ | 2,3,5-trimethoxyphenyl | |
| 126 | SC(S)NR'R | CH₃ | 2,3,6-trimethoxyphenyl | |
| 127 | SC(S)NR'R | CH₃ | 2,4,5-trichlorophenyl | |
| 128 | SC(S)NR'R | CH₃ | 2,4,6-trichlorophenyl | |
| 129 | SC(S)NR'R | CH₃ | 2,3,4,6-tetrachlorophenyl | |
| 130 | SC(S)NR'R | CH₃ | 2,3,5,6-tetrachlorophenyl | |
| 131 | SC(S)NR'R | CH₃ | 2-bromophenyl | |
| 132 | SC(S)NR'R | CH₃ | 3-bromophenyl | |
| 133 | SC(S)NR'R | CH₃ | 4-bromophenyl | |
| 134 | SC(S)NR'R | CH₃ | 2,4-dibromophenyl | |
| 135 | SC(S)NR'R | CH₃ | 3-bromo-4-fluorophenyl | |
| 136 | SC(S)NR'R | CH₃ | 3-bromo-4-methoxyphenyl | |

TABLE 1-continued

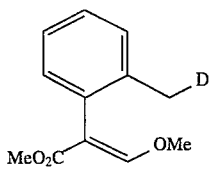

| No. | D | R' | R | phys. data[a] |
|---|---|---|---|---|
| 137 | SC(S)NR'R | CH₃ | 2-iodophenyl | |
| 138 | SC(S)NR'R | CH₃ | 3-iodophenyl | |
| 139 | SC(S)NR'R | CH₃ | 4-iodophenyl | |
| 140 | SC(S)NR'R | CH₃ | 2-chloro-4-fluorophenyl | |
| 141 | SC(S)NR'R | CH₃ | 2-chloro-5-fluorophenyl | |
| 142 | SC(S)NR'R | CH₃ | 2-chloro-6-fluorophenyl | |
| 143 | SC(S)NR'R | CH₃ | 2-chloro-4-bromophenyl | |
| 144 | SC(S)NR'R | CH₃ | 2-bromo-4-chlorophenyl | |
| 145 | SC(S)NR'R | CH₃ | 2-bromo-4-fluorophenyl | |
| 146 | SC(S)NR'R | CH₃ | 3-bromo-4-chlorophenyl | |
| 147 | SC(S)NR'R | CH₃ | 3-chloro-4-fluorophenyl | |
| 148 | SC(S)NR'R | CH₃ | 3-fluoro-4-chlorophenyl | |
| 149 | SC(S)NR'R | CH₃ | 2-cyanophenyl | |
| 150 | SC(S)NR'R | CH₃ | 3-cyanophenyl | |
| 151 | SC(S)NR'R | CH₃ | 4-cyanophenyl | |
| 152 | SC(S)NR'R | CH₃ | 2-nitrophenyl | |
| 153 | SC(S)NR'R | CH₃ | 3-nitrophenyl | |
| 154 | SC(S)NR'R | CH₃ | 4-nitrophenyl | |
| 155 | SC(S)NR'R | CH₃ | 2-methylphenyl | |
| 156 | SC(S)NR'R | CH₃ | 3-methylphenyl | |
| 157 | SC(S)NR'R | CH₃ | 4-methylphenyl | |
| 158 | SC(S)NR'R | CH₃ | 2,4-dimethylphenyl | |
| 159 | SC(S)NR'R | CH₃ | 2,6-dimethylphenyl | |
| 160 | SC(S)NR'R | CH₃ | 3,4-dimethylphenyl | |
| 161 | SC(S)NR'R | CH₃ | 3,5-dimethylphenyl | |
| 162 | SC(S)NR'R | CH₃ | 2,3,4-trimethylphenyl | |
| 163 | SC(S)NR'R | CH₃ | 2,3,5-trimethylphenyl | |
| 164 | SC(S)NR'R | CH₃ | 2,3,6-trimethylphenyl | |
| 165 | SC(S)NR'R | CH₃ | 2,4,5-trimethylphenyl | |
| 166 | SC(S)NR'R | CH₃ | 2,4,6-trimethylphenyl | |
| 167 | SC(S)NR'R | CH₃ | 2,4,5-trimethylphenyl | |
| 168 | SC(S)NR'R | CH₃ | pentamethylphenyl | |
| 169 | SC(S)NR'R | CH₃ | 2-ethylphenyl | |
| 170 | SC(S)NR'R | CH₃ | 3-ethylphenyl | |
| 171 | SC(S)NR'R | CH₃ | 4-ethylphenyl | |
| 172 | SC(S)NR'R | CH₃ | 3,5-diethylphenyl | |
| 173 | SC(S)NR'R | CH₃ | 2-n-propylphenyl | |
| 174 | SC(S)NR'R | CH₃ | 3-n-propylphenyl | |
| 175 | SC(S)NR'R | CH₃ | 4-n-propylphenyl | |
| 176 | SC(S)NR'R | CH₃ | 2,4,5-trimethoxyphenyl | |
| 177 | SC(S)NR'R | CH₃ | 2,4,6-trimethoxyphenyl | |
| 178 | SC(S)NR'R | CH₃ | 3,4,5-trimethoxyphenyl | |
| 179 | SC(S)NR'R | CH₃ | 2-ethoxyphenyl | |
| 180 | SC(S)NR'R | CH₃ | 3-ethoxyphenyl | |
| 181 | SC(S)NR'R | CH₃ | 4-ethoxyphenyl | |
| 182 | SC(S)NR'R | CH₃ | 2-isopropoxyphenyl | |
| 183 | SC(S)NR'R | CH₃ | 3-isopropoxyphenyl | |
| 184 | SC(S)NR'R | CH₃ | 4-isopropoxyphenyl | |
| 185 | SC(S)NR'R | CH₃ | 3-tert.-butoxyphenyl | |
| 186 | SC(S)NR'R | CH₃ | 4-tert.-butoxyphenyl | |
| 187 | SC(S)NR'R | CH₃ | 2-trifluoromethoxyphenyl | |
| 188 | SC(S)NR'R | CH₃ | 3-trifluoromethoxyphenyl | |
| 189 | SC(S)NR'R | CH₃ | 4-trifluoromethoxyphenyl | |
| 190 | SC(S)NR'R | CH₃ | 3-(1',1',2',2'-tetra-fluoro)-ethoxyphenyl | |
| 191 | SC(S)NR'R | CH₃ | 4-(1',1',2',2'-tetra-fluoro)-ethoxyphenyl | |
| 192 | SC(S)NR'R | CH₃ | 2-chloromethylphenyl | |
| 193 | SC(S)NR'R | CH₃ | 3-chloromethylphenyl | |
| 194 | SC(S)NR'R | CH₃ | 4-chloromethylphenyl | |
| 195 | SC(S)NR'R | CH₃ | 2-trifluoromethylphenyl | |
| 196 | SC(S)NR'R | CH₃ | 3-trifluoromethylphenyl | |
| 197 | SC(S)NR'R | CH₃ | 4-trifluoromethylphenyl | |
| 198 | SC(S)NR'R | CH₃ | 2-(methoxyiminomethyl)-phenyl | |
| 199 | SC(S)NR'R | CH₃ | 3-(methoxyiminomethyl)-phenyl | |
| 200 | SC(S)NR'R | CH₃ | 4-(methoxyiminomethyl)-phenyl | |
| 201 | SC(S)NR'R | CH₃ | 2-(ethoxyiminomethyl)-phenyl | |
| 202 | SC(S)NR'R | CH₃ | 3-(ethoxyiminomethyl)-phenyl | |
| 203 | SC(S)NR'R | CH₃ | 4-(ethoxyiminomethyl)-phenyl | |
| 204 | SC(S)NR'R | CH₃ | 2-methyl-4-methoximinoethyl-phenyl | |
| 205 | SC(S)NR'R | CH₃ | 2-methyl-4-methoximinomethyl-phenyl | |

TABLE 1-continued

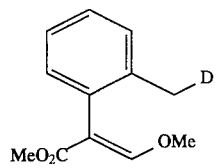

| No. | D | R' | R | phys. data[a)] |
|---|---|---|---|---|
| 206 | SC(S)NR'R | CH₃ | 2,6-dimethyl-4-methoximinomethyl-phenyl | |
| 207 | SC(S)NR'R | CH₃ | 2,6-dimethyl-4-methoximinoethyl-phenyl | |
| 208 | SC(S)NR'R | CH₃ | 2-phenylphenyl | |
| 209 | SC(S)NR'R | CH₃ | 3-phenylphenyl | |
| 210 | SC(S)NR'R | CH₃ | 4-phenylphenyl | |
| 211 | SC(S)NR'R | CH₃ | 2-phenoxyphenyl | |
| 212 | SC(S)NR'R | CH₃ | 3-phenoxyphenyl | |
| 213 | SC(S)NR'R | CH₃ | 4-phenoxyphenyl | |
| 214 | SC(S)NR'R | CH₃ | 2-benzyloxyphenyl | |
| 215 | SC(S)NR'R | CH₃ | 3-benzyloxyphenyl | |
| 216 | SC(S)NR'R | CH₃ | 4-benzyloxyphenyl | |
| 217 | SC(S)NR'R | CH₃ | 4-(imidazol-1'-yl)phenyl | |
| 218 | SC(S)NR'R | CH₃ | 4-(piperazin-1'-yl)phenyl | |
| 219 | SC(S)NR'R | CH₃ | 4-(morpholin-1'-yl)phenyl | |
| 220 | SC(S)NR'R | CH₃ | 4-(piperidin-1'-yl)phenyl | |
| 221 | SC(S)NR'R | CH₃ | 4-(pyridyl-2'-oxy)phenyl | |
| 222 | SC(S)NR'R | CH₃ | 2-cyclopropylphenyl | |
| 223 | SC(S)NR'R | CH₃ | 3-cyclopropylphenyl | |
| 224 | SC(S)NR'R | CH₃ | 4-cyclopropylphenyl | |
| 225 | SC(S)NR'R | CH₃ | 3-cyclohexylphenyl | |
| 226 | SC(S)NR'R | CH₃ | 4-cyclohexylphenyl | |
| 227 | SC(S)NR'R | CH₃ | 4-oxiranylphenyl | |
| 228 | SC(S)NR'R | CH₃ | 4-(1',3'-dioxan-2'-yl)-phenyl | |
| 229 | SC(S)NR'R | CH₃ | 4-(tetrahydropyran-2-yl-oxy)-phenyl | |
| 230 | SC(S)NR'R | CH₃ | 1-naphthyl | |
| 231 | SC(S)NR'R | CH₃ | 2-naphthyl | |
| 232 | SC(S)NR'R | CH₃ | benzyl | 4.50 (CH₂) amide rotamers |
| 233 | SC(S)NR'R | CH₃ | 2-methylbenzyl | |
| 234 | SC(S)NR'R | CH₃ | 3-methylbenzyl | |
| 235 | SC(S)NR'R | CH₃ | 4-methylbenzyl | |
| 236 | SC(S)NR'R | CH₃ | 4-tert.-butylbenzyl | 1.31(9H), 4.50(CH₂) amide rotamers |
| 237 | SC(S)NR'R | CH₃ | 2-chlorobenzyl | |
| 238 | SC(S)NR'R | CH₃ | 3-chlorobenzyl | |
| 239 | SC(S)NR'R | CH₃ | 4-chlorobenzyl | |
| 240 | SC(S)NR'R | CH₃ | 2-pyridyl | |
| 241 | SC(S)NR'R | CH₃ | 3-pyridyl | |
| 242 | SC(S)NR'R | CH₃ | 4-pyridyl | |
| 243 | SC(S)NR'R | CH₃ | 2,6-pyrimidinyl | |
| 244 | SC(S)NR'R | CH₃ | 1,5-pyrimidinyl | |
| 245 | SC(S)NR'R | CH₃ | 2-thienyl | |
| 246 | SC(S)NR'R | CH₃ | 3-thienyl | |
| 247 | SC(S)NR'R | CH₃ | 2-furyl | |
| 248 | SC(S)NR'R | CH₃ | 3-furyl | |
| 249 | SC(S)NR'R | CH₃ | 1-pyrrolyl | |
| 250 | SC(S)NR'R | CH₃ | 1-imidazolyl | |
| 251 | SC(S)NR'R | CH₃ | 1,2,4-triazolyl | |
| 252 | SC(S)NR'R | CH₃ | 1,3,4-triazolyl | |
| 253 | SC(S)NR'R | CH₃ | 4-thiazolyl | |
| 254 | SC(S)NR'R | CH₃ | 2-benzothiazolyl | |
| 255 | SC(S)NR'R | CH₃ | 2-pyridylmethyl | |
| 256 | SC(S)NR'R | CH₃ | 3-pyridylmethyl | |
| 257 | SC(S)NR'R | CH₃ | 4-pyridylmethyl | |
| 258 | SC(S)NR'R | Et | phenyl | 1.26(9H), 3.57, 3.72(3H), 4.24(2 × 2H) |
| 259 | SC(S)NR'R | Et | 2-methylphenyl | |
| 260 | SC(S)NR'R | Et | 2-chlorophenyl | |
| 261 | SC(S)NR'R | Et | 4-methylphenyl | 107–112° C. |
| 262 | SC(S)NR'R | Et | 2-naphtyl | |
| 263 | SC(S)SR | — | CH₃ | |
| 264 | SC(S)SR | — | CH₂-phenyl | |
| 265 | SC(S)SR | — | phenyl | |
| 266 | SC(S)SR | — | A* | 3.67, 3.77(3H), 4.55(2H), 7.39(1H) |
| 267 | SC(S)OR | — | CH₃ | |
| 268 | SC(S)OR | — | phenyl | |
| 269 | SC(S)OR | — | 2-CH₃-phenyl | |
| 270 | SC(S)OR | — | 3-CH₃-phenyl | 2.38, 3.71, 3.84(3H), 4.39(2H) |
| 271 | SC(S)OR | — | 4-CH₃-phenyl | |
| 272 | SC(S)OR | — | 2-Cl-phenyl | |
| 273 | SC(S)OR | — | 3-Cl-phenyl | |
| 274 | SC(S)OR | — | 4-Cl-phenyl | |

TABLE 1-continued

| No. | D | R' | R | phys. data[a] |
|-----|---|----|----|---------------|
| 275 | SC(S)OR | — | CH$_2$-phenyl | 1707, 1633, 1256, 1197, 1126, 1054 |
| 276 | SC(S)OR | — | CH$_2$—(2-Me)-phenyl | 2.35, 3.69, 3.81(3H), 4.32, 5.63(2H), 7.58(1H) |
| 277 | SC(S)OR | — | CH$_2$—(3-Me)-phenyl | |
| 278 | SC(S)OR | — | CH$_2$—(4-Me)-phenyl | |
| 279 | SC(S)OR | — | CH$_2$—(2-Cl)-phenyl | 1746, 1462, 1255, 1127, 1060 |
| 280 | SC(S)OR | — | CH$_2$—(3-Cl)phenyl | |
| 281 | SC(S)OR | — | CH$_2$—(4-Cl)phenyl | |
| 282 | OC(O)OR | — | CH$_3$ | |
| 283 | OC(O)OR | — | tert.-butyl | |
| 284 | OC(O)OR | — | CH$_2$-phenyl | |
| 285 | OC(O)OR | — | phenyl | |
| 286 | SC(S)NR'R | CH$_3$ | 3-Me, 4-F-phenyl | 2.25; 3.57; 3.72; 3.75(4 × 3H); 4.35(2H); 7.00–7.41(7H); 7.51(1H) |
| 287 | SC(S)NR'R | H | 2-phenyl-eth-2-yl | 7.58(1H) amide rotamers |
| 288 | SC(S)NR'R | Me | 4-tert-butoxybenzyl | 98–102° C. |
| 289 | SC(S)NR'R | Et | 3,4-(—OCH$_2$O—)phenyl | 130–134° C. |
| 290 | SC(S)OR | — | ethyl | 1708, 1633, 1257, 1126, 1048 |
| 291 | SC(S)OR | — | isopropyl | 1707, 1632, 1250, 1226, 1224, 1089, 1037 |
| 292 | SC(S)OR | — | 4-methoxybenzyl | 3.70, 3.80, 3.83(3H), 4.57(2H), 7.58(1H) |
| 293 | SC(S)NR'R | Me | CH$_2$—(3-pyridyl) | 1705, 1633, 1480, 1432, 1384, 1258, 1198, 1125, 989 |

A* = 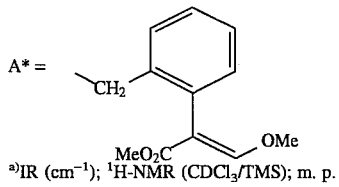

[a] IR (cm$^{-1}$); $^1$H-NMR (CDCl$_3$/TMS); m. p.

TABLE 2

| No. | D | R' | R | phys. data[a] |
|-----|---|----|----|---------------|
| 1 | SC(S)NR'R | CH$_3$ | methyl | |
| 2 | SC(S)NR'R | CH$_3$ | ethyl | |
| 3 | SC(S)NR'R | CH$_3$ | n-propyl | |
| 4 | SC(S)NR'R | CH$_3$ | tert.-butyl | |
| 5 | SC(S)NR'R | CH$_3$ | cyclopropyl | |
| 6 | SC(S)NR'R | CH$_3$ | cyclohexyl | 2934, 1727, 1473, 1439, 1393, 1319, 1216, 1087, 1067, 1017 |
| 7 | SC(S)NR'R | CH$_3$ | methoxymethyl | |
| 8 | SC(S)NR'R | CH$_3$ | phenoxymethyl | |
| 9 | SC(S)NR'R | CH$_3$ | methylthiomethyl | |
| 10 | SC(S)NR'R | CH$_3$ | phenyl | 3.75; 3.76; 3.95 (3 × 3H); 4.32(2H); 7.08–7.51 (9H); |
| 11 | SC(S)NR'R | CH$_3$ | 2-fluorophenyl | |
| 12 | SC(S)NR'R | CH$_3$ | 3-fluorophenyl | 3.73; 3.80; 3.99 (3 × 3H); 4.33 (2H); 6.95–7.50 (8H) |
| 13 | SC(S)NR'R | CH$_3$ | 4-fluorophenyl | 3.72; 3.77; 3.97 (3 × 3H); 4.32 (2H); 7.07–7.48 (8H) |
| 14 | SC(S)NR'R | CH$_3$ | pentafluorophenyl | |
| 15 | SC(S)NR'R | CH$_3$ | 2-chlorophenyl | |
| 16 | SC(S)NR'R | CH$_3$ | 3-chlorophenyl | 3.72; 3.80; 3.97 (3 × 3H); 4.34 (2H); 7.10–7.49 (8H) |
| 17 | SC(S)NR'R | CH$_3$ | 4-chlorophenyl | 2.91, 3.72, 4.05 (3H), 4.30 (2H), 6.57–7.40 ppm (8H) |

TABLE 2-continued

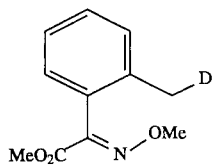

| No. | D | R' | R | phys. data[a] |
|---|---|---|---|---|
| 18 | SC(S)NR'R | CH$_3$ | pentachlorophenyl | |
| 19 | SC(S)NR'R | CH$_3$ | 2,3-dichlorophenyl | |
| 20 | SC(S)NR'R | CH$_3$ | 2,4-dichlorophenyl | |
| 21 | SC(S)NR'R | CH$_3$ | 2,5-dichlorophenyl | |
| 22 | SC(S)NR'R | CH$_3$ | 2,6-dichlorophenyl | |
| 23 | SC(S)NR'R | CH$_3$ | 3,4-dichlorophenyl | |
| 24 | SC(S)NR'R | CH$_3$ | 3,5-dichlorophenyl | |
| 25 | SC(S)NR'R | CH$_3$ | 2,3,4-trichlorophenyl | |
| 26 | SC(S)NR'R | CH$_3$ | 2,3,5-trichlorophenyl | |
| 27 | SC(S)NR'R | CH$_3$ | 2,3,6-trichlorophenyl | |
| 28 | SC(S)NR'R | CH$_3$ | 2,4,5-trichlorophenyl | |
| 29 | SC(S)NR'R | CH$_3$ | 2,4,6-trichlorophenyl | |
| 30 | SC(S)NR'R | CH$_3$ | 3,4,5-trichlorophenyl | |
| 31 | SC(S)NR'R | CH$_3$ | 2,3,4,6-tetrachlorophenyl | |
| 32 | SC(S)NR'R | CH$_3$ | 2,3,5,6-tetrachlorophenyl | |
| 33 | SC(S)NR'R | CH$_3$ | 2-bromophenyl | |
| 34 | SC(S)NR'R | CH$_3$ | 3-bromophenyl | |
| 35 | SC(S)NR'R | CH$_3$ | 4-bromophenyl | |
| 36 | SC(S)NR'R | CH$_3$ | 2,4-dibromophenyl | |
| 37 | SC(S)NR'R | CH$_3$ | 3-bromo-4-fluorophenyl | |
| 38 | SC(S)NR'R | CH$_3$ | 3-bromo-4-methoxyphenyl | |
| 39 | SC(S)NR'R | CH$_3$ | 2-iodophenyl | |
| 40 | SC(S)NR'R | CH$_3$ | 3-iodophenyl | |
| 41 | SC(S)NR'R | CH$_3$ | 4-iodophenyl | |
| 42 | SC(S)NR'R | CH$_3$ | 2-chloro-4-fluorophenyl | |
| 43 | SC(S)NR'R | CH$_3$ | 2-chloro-5-fluorophenyl | |
| 44 | SC(S)NR'R | CH$_3$ | 2-chloro-6-fluorophenyl | |
| 45 | SC(S)NR'R | CH$_3$ | 2-chloro-4-bromophenyl | |
| 46 | SC(S)NR'R | CH$_3$ | 2-bromo-4-chlorophenyl | |
| 47 | SC(S)NR'R | CH$_3$ | 2-bromo-4-fluorophenyl | |
| 48 | SC(S)NR'R | CH$_3$ | 3-bromo-4-fluorophenyl | |
| 49 | SC(S)NR'R | CH$_3$ | 3-chloro-4-fluorophenyl | |
| 50 | SC(S)NR'R | CH$_3$ | 3-fluoro-4-chlorophenyl | |
| 51 | SC(S)NR'R | CH$_3$ | 2-cyanophenyl | |
| 52 | SC(S)NR'R | CH$_3$ | 3-cyanophenyl | |
| 53 | SC(S)NR'R | CH$_3$ | 4-cyanophenyl | |
| 54 | SC(S)NR'R | CH$_3$ | 2-nitrophenyl | |
| 55 | SC(S)NR'R | CH$_3$ | 3-nitrophenyl | |
| 56 | SC(S)NR'R | CH$_3$ | 4-nitrophenyl | |
| 57 | SC(S)NR'R | CH$_3$ | 2-methylphenyl | 2.17; 3.69; 3.76; 3.95; (4 × 3H); 4.33 (2H); 7.06–7.50 (8H) |
| 58 | SC(S)NR'R | CH$_3$ | 3-methylphenyl | 2.36; 3.74; 3.77; 3.96; (4 × 3H); 4.32 (2H); 6.98–7.48 (8H) |
| 59 | SC(S)NR'R | CH$_3$ | 4-methylphenyl | 2.35; 3.72; 3.77; 3.97; (4 × 3H); 4.30 (2H); 7.07–7.47 (8H) |
| 60 | SC(S)NR'R | CH$_3$ | 2,4-dimethylphenyl | |
| 61 | SC(S)NR'R | CH$_3$ | 2,6-dimethylphenyl | |
| 62 | SC(S)NR'R | CH$_3$ | 3,4-dimethylphenyl | |
| 63 | SC(S)NR'R | CH$_3$ | 3,5-dimethylphenyl | |
| 64 | SC(S)NR'R | CH$_3$ | 2,3,4-trimethylphenyl | |
| 65 | SC(S)NR'R | CH$_3$ | 2,3,5-trimethylphenyl | |
| 66 | SC(S)NR'R | CH$_3$ | 2,3,6-trimethylphenyl | |
| 67 | SC(S)NR'R | CH$_3$ | 2,4,5-trimethylphenyl | |
| 68 | SC(S)NR'R | CH$_3$ | 2,4,6-trimethylphenyl | |
| 69 | SC(S)NR'R | CH$_3$ | 3,4,5-trimethylphenyl | |
| 70 | SC(S)NR'R | CH$_3$ | pentamethylphenyl | |
| 71 | SC(S)NR'R | CH$_3$ | 2-ethylphenyl | |
| 72 | SC(S)NR'R | CH$_3$ | 3-ethylphenyl | |
| 73 | SC(S)NR'R | CH$_3$ | 4-ethylphenyl | |
| 74 | SC(S)NR'R | CH$_3$ | 3,5-diethylphenyl | |
| 75 | SC(S)NR'R | CH$_3$ | 2-n-propylphenyl | |
| 76 | SC(S)NR'R | CH$_3$ | 3-n-propylphenyl | |
| 77 | SC(S)NR'R | CH$_3$ | 4-n-propylphenyl | |
| 78 | SC(S)NR'R | CH$_3$ | 2-isopropylphenyl | |
| 79 | SC(S)NR'R | CH$_3$ | 3-isopropylphenyl | |
| 80 | SC(S)NR'R | CH$_3$ | 4-isopropylphenyl | |
| 81 | SC(S)NR'R | CH$_3$ | 2,4-diisopropylphenyl | |
| 82 | SC(S)NR'R | CH$_3$ | 3,5-diisopropylphenyl | |
| 83 | SC(S)NR'R | CH$_3$ | 4-n-butyphenyl | |

TABLE 2-continued

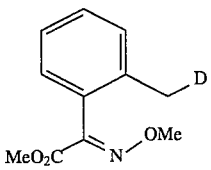

| No. | D | R' | R | phys. data[a] |
|---|---|---|---|---|
| 84 | SC(S)NR'R | CH$_3$ | 4-sec.-butylphenyl | |
| 85 | SC(S)NR'R | CH$_3$ | 4-isobutylphenyl | |
| 86 | SC(S)NR'R | CH$_3$ | 4-tert.-butylphenyl | |
| 87 | SC(S)NR'R | CH$_3$ | 3-tert.-butylphenyl | |
| 88 | SC(S)NR'R | CH$_3$ | 2-tert.-butylphenyl | |
| 89 | SC(S)NR'R | CH$_3$ | 2,4-di-tert.-butylphenyl | |
| 90 | SC(S)NR'R | CH$_3$ | 3,5-di-tert.-butylphenyl | |
| 91 | SC(S)NR'R | CH$_3$ | 4-n-hexylphenyl | |
| 92 | SC(S)NR'R | CH$_3$ | 4-n-dodecylphenyl | |
| 93 | SC(S)NR'R | CH$_3$ | 2-methyl-4-tert.-butylphenyl | |
| 94 | SC(S)NR'R | CH$_3$ | 2-methyl-6-tert.-butylphenyl | |
| 95 | SC(S)NR'R | CH$_3$ | 2-methyl-4-isopropylphenyl | |
| 96 | SC(S)NR'R | CH$_3$ | 2-methyl-4-cyclohexylphenyl | |
| 97 | SC(S)NR'R | CH$_3$ | 2-methyl-4-phenylphenyl | |
| 98 | SC(S)NR'R | CH$_3$ | 2-methyl-4-benzylphenyl | |
| 99 | SC(S)NR'R | CH$_3$ | 2-methyl-4-phenoxyphenyl | |
| 100 | SC(S)NR'R | CH$_3$ | 2-methyl-4-benzyloxyphenyl | |
| 101 | SC(S)NR'R | CH$_3$ | 2-methyl-3-chlorophenyl | |
| 102 | SC(S)NR'R | CH$_3$ | 2-methyl-4-chlorophenyl | |
| 103 | SC(S)NR'R | CH$_3$ | 2-methyl-5-chlorophenyl | |
| 104 | SC(S)NR'R | CH$_3$ | 2-methyl-6-chlorophenyl | |
| 105 | SC(S)NR'R | CH$_3$ | 2-methyl-4-fluorophenyl | |
| 106 | SC(S)NR'R | CH$_3$ | 2-methyl-3-bromophenyl | |
| 107 | SC(S)NR'R | CH$_3$ | 2-methyl-4-bromophenyl | |
| 108 | SC(S)NR'R | CH$_3$ | 2-methyl-3-methoxyphenyl | |
| 109 | SC(S)NR'R | CH$_3$ | 2-methyl-4-methoxyphenyl | |
| 110 | SC(S)NR'R | CH$_3$ | 2-methyl-5-methoxyphenyl | |
| 111 | SC(S)NR'R | CH$_3$ | 2-methyl-6-methoxyphenyl | |
| 112 | SC(S)NR'R | CH$_3$ | 2-methyl-4-isopropoxyphenyl | |
| 113 | SC(S)NR'R | CH$_3$ | 2-methyl-2,5-dimethoxyphenyl | |
| 114 | SC(S)NR'R | CH$_3$ | 2-methoxyphenyl | |
| 115 | SC(S)NR'R | CH$_3$ | 3-methoxyphenyl | |
| 116 | SC(S)NR'R | CH$_3$ | 4-methoxyphenyl | |
| 117 | SC(S)NR'R | CH$_3$ | 2,3-dimethoxyphenyl | |
| 118 | SC(S)NR'R | CH$_3$ | 2,4-dimethoxyphenyl | |
| 119 | SC(S)NR'R | CH$_3$ | 2,5-dimethoxyphenyl | |
| 120 | SC(S)NR'R | CH$_3$ | 2,6-dimethoxyphenyl | |
| 121 | SC(S)NR'R | CH$_3$ | 3,4-dimethoxyphenyl | |
| 122 | SC(S)NR'R | CH$_3$ | 3,5-dimethoxyphenyl | |
| 123 | SC(S)NR'R | CH$_3$ | 3,6-dimethoxyphenyl | |
| 124 | SC(S)NR'R | CH$_3$ | 2,3,4-trimethoxyphenyl | |
| 125 | SC(S)NR'R | CH$_3$ | 2,3,5-trimethoxyphenyl | |
| 126 | SC(S)NR'R | CH$_3$ | 2,3,6-trimethoxyphenyl | |
| 127 | SC(S)NR'R | CH$_3$ | 2,4,5-trichlorophenyl | |
| 128 | SC(S)NR'R | CH$_3$ | 2,4,6-trichloroyphenyl | |
| 129 | SC(S)NR'R | CH$_3$ | 2,3,4,6-tetrachlorophenyl | |
| 130 | SC(S)NR'R | CH$_3$ | 2,3,5,6-tetrachlorophenyl | |
| 131 | SC(S)NR'R | CH$_3$ | 2-bromophenyl | |
| 132 | SC(S)NR'R | CH$_3$ | 3-bromophenyl | |
| 133 | SC(S)NR'R | CH$_3$ | 4-bromophenyl | |
| 134 | SC(S)NR'R | CH$_3$ | 2,4-dibromophenyl | |
| 135 | SC(S)NR'R | CH$_3$ | 3-bromo-4-fluorophenyl | |
| 136 | SC(S)NR'R | CH$_3$ | 3-bromo-4-methoxyphenyl | |
| 137 | SC(S)NR'R | CH$_3$ | 2-iodophenyl | |
| 138 | SC(S)NR'R | CH$_3$ | 3-iodophenyl | |
| 139 | SC(S)NR'R | CH$_3$ | 4-iodophenyl | |
| 140 | SC(S)NR'R | CH$_3$ | 2-chloro-4-fluorophenyl | |
| 141 | SC(S)NR'R | CH$_3$ | 2-chloro-5-fluorophenyl | |
| 142 | SC(S)NR'R | CH$_3$ | 2-chloro-6-fluorophenyl | |
| 143 | SC(S)NR'R | CH$_3$ | 2-chloro-4-bromophenyl | |
| 144 | SC(S)NR'R | CH$_3$ | 2-bromo-4-chlorophenyl | |
| 145 | SC(S)NR'R | CH$_3$ | 2-bromo-4-fluorophenyl | |
| 146 | SC(S)NR'R | CH$_3$ | 3-bromo-4-chlorophenyl | |
| 147 | SC(S)NR'R | CH$_3$ | 3-chloro-4-fluorophenyl | |
| 148 | SC(S)NR'R | CH$_3$ | 3-fluoro-4-chlorophenyl | |
| 149 | SC(S)NR'R | CH$_3$ | 2-cyanophenyl | |
| 150 | SC(S)NR'R | CH$_3$ | 3-cyanophenyl | |
| 151 | SC(S)NR'R | CH$_3$ | 4-cyanophenyl | |
| 152 | SC(S)NR'R | CH$_3$ | 2-nitrophenyl | |

TABLE 2-continued

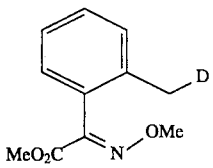

| No. | D | R' | R | phys. data[a] |
|---|---|---|---|---|
| 153 | SC(S)NR'R | CH$_3$ | 3-nitrophenyl | |
| 154 | SC(S)NR'R | CH$_3$ | 4-nitrophenyl | |
| 155 | SC(S)NR'R | CH$_3$ | 2-methylphenyl | |
| 156 | SC(S)NR'R | CH$_3$ | 3-methylphenyl | |
| 157 | SC(S)NR'R | CH$_3$ | 4-methylphenyl | |
| 158 | SC(S)NR'R | CH$_3$ | 2,4-dimethylphenyl | |
| 159 | SC(S)NR'R | CH$_3$ | 2,6-dimethylphenyl | |
| 160 | SC(S)NR'R | CH$_3$ | 3,4-dimethylphenyl | |
| 161 | SC(S)NR'R | CH$_3$ | 3,5-dimethylphenyl | |
| 162 | SC(S)NR'R | CH$_3$ | 2,3,4-trimethylphenyl | |
| 163 | SC(S)NR'R | CH$_3$ | 2,3,5-trimethylphenyl | |
| 164 | SC(S)NR'R | CH$_3$ | 2,3,6-trimethylphenyl | |
| 165 | SC(S)NR'R | CH$_3$ | 2,4,5-trimethylphenyl | |
| 166 | SC(S)NR'R | CH$_3$ | 2,4,6-trimethylphenyl | |
| 167 | SC(S)NR'R | CH$_3$ | 2,4,5-trimethylphenyl | |
| 168 | SC(S)NR'R | CH$_3$ | pentamethylphenyl | |
| 169 | SC(S)NR'R | CH$_3$ | 2-ethylphenyl | |
| 170 | SC(S)NR'R | CH$_3$ | 3-ethylphenyl | |
| 171 | SC(S)NR'R | CH$_3$ | 4-ethylphenyl | |
| 172 | SC(S)NR'R | CH$_3$ | 3,5-diethylphenyl | |
| 173 | SC(S)NR'R | CH$_3$ | 2-n-propylphenyl | |
| 174 | SC(S)NR'R | CH$_3$ | 3-n-propylphenyl | |
| 175 | SC(S)NR'R | CH$_3$ | 4-n-propylphenyl | |
| 176 | SC(S)NR'R | CH$_3$ | 2,4,5-trimethoxyphenyl | |
| 177 | SC(S)NR'R | CH$_3$ | 2,4,6-trimethoxyphenyl | |
| 178 | SC(S)NR'R | CH$_3$ | 3,4,5-trimethoxyphenyl | |
| 179 | SC(S)NR'R | CH$_3$ | 2-ethoxyphenyl | |
| 180 | SC(S)NR'R | CH$_3$ | 3-ethoxyphenyl | |
| 181 | SC(S)NR'R | CH$_3$ | 4-ethoxyphenyl | |
| 182 | SC(S)NR'R | CH$_3$ | 2-isopropoxyphenyl | |
| 183 | SC(S)NR'R | CH$_3$ | 3-isopropoxyphenyl | |
| 184 | SC(S)NR'R | CH$_3$ | 4-isopropoxyphenyl | |
| 185 | SC(S)NR'R | CH$_3$ | 3-tert.-butoxyphenyl | |
| 186 | SC(S)NR'R | CH$_3$ | 4-tert.-butoxyphenyl | |
| 187 | SC(S)NR'R | CH$_3$ | 2-trifluoromethoxyphenyl | |
| 188 | SC(S)NR'R | CH$_3$ | 3-trifluoromethoxyphenyl | |
| 189 | SC(S)NR'R | CH$_3$ | 4-trifluoromethoxyphenyl | |
| 190 | SC(S)NR'R | CH$_3$ | 3-(1',1',2',2'-tetra-fluoro)-ethoxyphenyl | |
| 191 | SC(S)NR'R | CH$_3$ | 4-(1',1',2',2'-tetra-fluoro)-ethoxyphenyl | |
| 192 | SC(S)NR'R | CH$_3$ | 2-chloromethylphenyl | |
| 193 | SC(S)NR'R | CH$_3$ | 3-chloromethylphenyl | |
| 194 | SC(S)NR'R | CH$_3$ | 4-chloromethylphenyl | |
| 195 | SC(S)NR'R | CH$_3$ | 2-trifluoromethylphenyl | |
| 196 | SC(S)NR'R | CH$_3$ | 3-trifluoromethylphenyl | |
| 197 | SC(S)NR'R | CH$_3$ | 4-trifluoromethylphenyl | |
| 198 | SC(S)NR'R | CH$_3$ | 2-(methoxyiminomethyl)-phenyl | |
| 199 | SC(S)NR'R | CH$_3$ | 3-(methoxyiminomethyl)-phenyl | |
| 200 | SC(S)NR'R | CH$_3$ | 4-(methoxyiminomethyl)-phenyl | |
| 201 | SC(S)NR'R | CH$_3$ | 2-(ethoxyiminomethyl)-phenyl | |
| 202 | SC(S)NR'R | CH$_3$ | 3-(ethoxyiminomethyl)-phenyl | |
| 203 | SC(S)NR'R | CH$_3$ | 4-(ethoxyiminomethyl)-phenyl | |
| 204 | SC(S)NR'R | CH$_3$ | 2-methyl-4-methoximinoethyl-phenyl | |
| 205 | SC(S)NR'R | CH$_3$ | 2-methyl-4-methoximinomethyl-phenyl | |
| 206 | SC(S)NR'R | CH$_3$ | 2,6-dimethyl-4-methoximino-methyl-phenyl | |
| 207 | SC(S)NR'R | CH$_3$ | 2,6-dimethyl-4-methoximino-ethyl-phenyl | |
| 208 | SC(S)NR'R | CH$_3$ | 2-phenylphenyl | |
| 209 | SC(S)NR'R | CH$_3$ | 3-phenylphenyl | |
| 210 | SC(S)NR'R | CH$_3$ | 4-phenylphenyl | |
| 211 | SC(S)NR'R | CH$_3$ | 2-phenoxyphenyl | |
| 212 | SC(S)NR'R | CH$_3$ | 3-phenoxyphenyl | |
| 213 | SC(S)NR'R | CH$_3$ | 4-phenoxyphenyl | |
| 214 | SC(S)NR'R | CH$_3$ | 2-benzyloxyphenyl | |
| 215 | SC(S)NR'R | CH$_3$ | 3-benzyloxyphenyl | |

TABLE 2-continued

| No. | D | R' | R | phys. data[a] |
|---|---|---|---|---|
| 216 | SC(S)NR'R | CH$_3$ | 4-benzyloxyphenyl | |
| 217 | SC(S)NR'R | CH$_3$ | 4-(imidazol-1'-yl)phenyl | |
| 218 | SC(S)NR'R | CH$_3$ | 4-(piperazin-1'-yl)phenyl | |
| 219 | SC(S)NR'R | CH$_3$ | 4-(morpholin-1'-yl)phenyl | |
| 220 | SC(S)NR'R | CH$_3$ | 4-(piperidin-1'-yl)phenyl | |
| 221 | SC(S)NR'R | CH$_3$ | 4-(pyridyl-2'-oxy)phenyl | |
| 222 | SC(S)NR'R | CH$_3$ | 2-cyclopropylphenyl | |
| 223 | SC(S)NR'R | CH$_3$ | 3-cyclopropylphenyl | |
| 224 | SC(S)NR'R | CH$_3$ | 4-cyclopropylphenyl | |
| 225 | SC(S)NR'R | CH$_3$ | 3-cyclohexylphenyl | |
| 226 | SC(S)NR'R | CH$_3$ | 4-cyclohexylphenyl | |
| 227 | SC(S)NR'R | CH$_3$ | 4-oxiranylphenyl | |
| 228 | SC(S)NR'R | CH$_3$ | 4-(1',3'-dioxan-2'-yl)-phenyl | |
| 229 | SC(S)NR'R | CH$_3$ | 4-(tetrahydropyran-2-yl-oxy)-phenyl | |
| 230 | SC(S)NR'R | CH$_3$ | 1-naphthyl | |
| 231 | SC(S)NR'R | CH$_3$ | 2-naphthyl | |
| 232 | SC(S)NR'R | CH$_3$ | benzyl | 84–90° C. |
| 233 | SC(S)NR'R | CH$_3$ | 2-methylbenzyl | |
| 234 | SC(S)NR'R | CH$_3$ | 3-methylbenzyl | |
| 235 | SC(S)NR'R | CH$_3$ | 4-methylbenzyl | |
| 236 | SC(S)NR'R | CH$_3$ | 4-tert.-butylbenzyl | 1.31 (9H), 4.50 (2H) amide rotamers |
| 237 | SC(S)NR'R | CH$_3$ | 2-chlorobenzyl | |
| 238 | SC(S)NR'R | CH$_3$ | 3-chlorobenzyl | |
| 239 | SC(S)NR'R | CH$_3$ | 4-chlorobenzyl | |
| 240 | SC(S)NR'R | CH$_3$ | 2-pyridyl | |
| 241 | SC(S)NR'R | CH$_3$ | 3-pyridyl | |
| 242 | SC(S)NR'R | CH$_3$ | 4-pyridyl | |
| 243 | SC(S)NR'R | CH$_3$ | 2,6-pyrimidinyl | |
| 244 | SC(S)NR'R | CH$_3$ | 1,5-pyrimidinyl | |
| 245 | SC(S)NR'R | CH$_3$ | 2-thienyl | |
| 246 | SC(S)NR'R | CH$_3$ | 3-thienyl | |
| 247 | SC(S)NR'R | CH$_3$ | 2-furyl | |
| 248 | SC(S)NR'R | CH$_3$ | 3-furyl | |
| 249 | SC(S)NR'R | CH$_3$ | 1-pyrrolyl | |
| 250 | SC(S)NR'R | CH$_3$ | 1-imidazolyl | |
| 251 | SC(S)NR'R | CH$_3$ | 1,2,4-triazolyl | |
| 252 | SC(S)NR'R | CH$_3$ | 1,3,4-triazolyl | |
| 253 | SC(S)NR'R | CH$_3$ | 4-thiazolyl | |
| 254 | SC(S)NR'R | CH$_3$ | 2-benzothiazolyl | |
| 255 | SC(S)NR'R | CH$_3$ | 2-pyridylmethyl | |
| 256 | SC(S)NR'R | CH$_3$ | 3-pyridylmethyl | |
| 257 | SC(S)NR'R | CH$_3$ | 4-pyridylmethyl | |
| 258 | SC(S)NR'R | Et | phenyl | 1.24 (3H), 3.76, 3.94 (3H), 4.03 (2 × CH$_2$) |
| 259 | SC(S)NR'R | Et | 2-methylphenyl | |
| 260 | SC(S)NR'R | Et | 2-chlorophenyl | |
| 261 | SC(S)NR'R | Et | 4-methylphenyl | 1633, 1523, 1508, 1444, 1399, 1305, 1272, 1103, 1038 |
| 262 | SC(S)NR'R | Et | 2-naphtyl | 110–114° C. |
| 263 | SC(S)SR | — | CH$_3$ | |
| 264 | SC(S)SR | — | CH$_2$-phenyl | |
| 265 | SC(S)SR | — | phenyl | |
| 266 | SC(S)SR | — | A* | 114–115° C. |
| 267 | SC(S)OR | — | CH$_3$ | 3.85, 4.04, 4.14 (3H); 4.25 (2H) |
| 268 | SC(S)OR | — | phenyl | |
| 269 | SC(S)OR | — | 2-CH$_3$-phenyl | |
| 270 | SC(S)OR | — | 3-CH$_3$-phenyl | |
| 271 | SC(S)OR | — | 4-CH$_3$-phenyl | |
| 272 | SC(S)OR | — | 2-Cl-phenyl | |
| 273 | SC(S)OR | — | 3-Cl-phenyl | |
| 274 | SC(S)OR | — | 4-Cl-phenyl | |
| 275 | SC(S)OR | — | CH$_2$-phenyl | |
| 276 | SC(S)OR | — | CH$_2$-(2-Me)-phenyl | 1727, 1436, 1218, 1066, 1017 |
| 277 | SC(S)OR | — | CH$_2$-(3-Me)-phenyl | 1727, 1437, 1218, 1066, 1018 |
| 278 | SC(S)OR | — | CH$_2$-(4-Me)-phenyl | |
| 279 | SC(S)OR | — | CH$_2$-(2-Cl)-phenyl | 1727, 1442, 1221, 1065, 1017 |
| 280 | SC(S)OR | — | CH$_2$-(3-Cl)phenyl | 3.86, 4.04 (3H), 4.28, 5.58 (2H) |
| 281 | SC(S)OR | — | CH$_2$-(4-Cl)phenyl | |
| 282 | OC(O)OR | — | CH$_3$ | |

TABLE 2-continued

| No. | D | R' | R | phys. data[a] |
|---|---|---|---|---|
| 283 | OC(O)OR | — | tert.-butyl | |
| 284 | OC(O)OR | — | CH$_2$-phenyl | |
| 285 | OC(O)OR | — | phenyl | |
| 286 | SC(S)NR'R | CH$_3$ | 3-Me, 4-F-phenyl | 2.27; 3.71; 3.78; 3.97 (4 × 3H); 4.32 (2H); 7.00–7.49 (7H) |
| 287 | SC(S)NR'R | H | 2-phenyl-eth-2-yl | 102–103° C. |
| 288 | SC(S)NR'R | Me | 4-tert-butoxybenzyl | 2975, 1726, 1656, 1482, 1387, 1236, 1216, 1161, 1066, 1017 |
| 289 | SC(S)NR'R | Et | 3,4-(-OCH$_2$O-)phenyl | 108–113° C. |
| 290 | SC(S)OR | — | ethyl | 1727, 1437, 1321, 1218, 1066, 1047, 1017 |
| 291 | SC(S)OR | — | isopropyl | 1726, 1436, 1218, 1090, 1066, 1040, 101 |
| 292 | SC(S)OR | — | benzyl | 3.87, 4.05 (3H), 4.27, 5.63 (2H) |

A* = 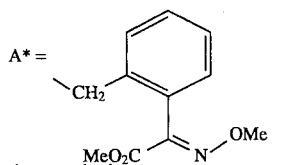

[a] IR (cm$^{-1}$); $^1$H-NMR (CDCl$_3$/TMS); m. p.

TABLE 3

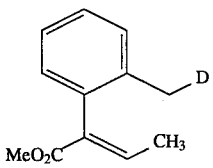 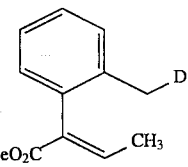

| No. | D | R' | R | phys. data[a] |
|---|---|---|---|---|
| 1 | SC(S)NR'R | CH$_3$ | methyl | |
| 2 | SC(S)NR'R | CH$_3$ | ethyl | |
| 3 | SC(S)NR'R | CH$_3$ | n-propyl | |
| 4 | SC(S)NR'R | CH$_3$ | tert.-butyl | |
| 5 | SC(S)NR'R | CH$_3$ | cyclopropyl | |
| 6 | SC(S)NR'R | CH$_3$ | cyclohexyl | |
| 7 | SC(S)NR'R | CH$_3$ | methoxymethyl | |
| 8 | SC(S)NR'R | CH$_3$ | phenoxymethyl | |
| 9 | SC(S)NR'R | CH$_3$ | methylthiomethyl | |
| 10 | SC(S)NR'R | CH$_3$ | phenyl | |
| 11 | SC(S)NR'R | CH$_3$ | 2-fluorophenyl | |
| 12 | SC(S)NR'R | CH$_3$ | 3-fluorophenyl | |
| 13 | SC(S)NR'R | CH$_3$ | 4-fluorophenyl | |
| 14 | SC(S)NR'R | CH$_3$ | pentafluorophenyl | |
| 15 | SC(S)NR'R | CH$_3$ | 2-chlorophenyl | |
| 16 | SC(S)NR'R | CH$_3$ | 3-chlorophenyl | |
| 17 | SC(S)NR'R | CH$_3$ | 4-chlorophenyl | |
| 18 | SC(S)NR'R | CH$_3$ | pentachlorophenyl | |
| 19 | SC(S)NR'R | CH$_3$ | 2,3-dichlorophenyl | |
| 20 | SC(S)NR'R | CH$_3$ | 2,,4-dichlorophenyl | |
| 21 | SC(S)NR'R | CH$_3$ | 2,5-dichlorophenyl | |
| 22 | SC(S)NR'R | CH$_3$ | 2,6-dichlorophenyl | |
| 23 | SC(S)NR'R | CH$_3$ | 3,4-dichlorophenyl | |
| 24 | SC(S)NR'R | CH$_3$ | 3,5-dichlorophenyl | |
| 25 | SC(S)NR'R | CH$_3$ | 2,3,4-trichlorophenyl | |
| 26 | SC(S)NR'R | CH$_3$ | 2,3,5-trichlorophenyl | |
| 27 | SC(S)NR'R | CH$_3$ | 2,3,6-trichlorophenyl | |
| 28 | SC(S)NR'R | CH$_3$ | 2,4,5-trichlorophenyl | |
| 29 | SC(S)NR'R | CH$_3$ | 2,4,6-trichlorophenyl | |
| 30 | SC(S)NR'R | CH$_3$ | 3,4,5-trichlorophenyl | |
| 31 | SC(S)NR'R | CH$_3$ | 2,3,4,6-tetrachlorophenyl | |
| 32 | SC(S)NR'R | CH$_3$ | 2,3,5,6-tetrachlorophenyl | |
| 33 | SC(S)NR'R | CH$_3$ | 2-bromophenyl | |
| 34 | SC(S)NR'R | CH$_3$ | 3-bromophenyl | |
| 35 | SC(S)NR'R | CH$_3$ | 4-bromophenyl | |
| 36 | SC(S)NR'R | CH$_3$ | 2,4-dibromophenyl | |
| 37 | SC(S)NR'R | CH$_3$ | 3-bromo-4-fluorophenyl | |
| 38 | SC(S)NR'R | CH$_3$ | 3-bromo-4-methoxyphenyl | |
| 39 | SC(S)NR'R | CH$_3$ | 2-iodophenyl | |
| 40 | SC(S)NR'R | CH$_3$ | 3-iodophenyl | |
| 41 | SC(S)NR'R | CH$_3$ | 4-iodophenyl | |
| 42 | SC(S)NR'R | CH$_3$ | 2-chloro-4-fluorophenyl | |
| 43 | SC(S)NR'R | CH$_3$ | 2-chloro-5-fluorophenyl | |
| 44 | SC(S)NR'R | CH$_3$ | 2-chloro-6-fluorophenyl | |
| 45 | SC(S)NR'R | CH$_3$ | 2-chloro-4-bromophenyl | |
| 46 | SC(S)NR'R | CH$_3$ | 2-bromo-4-chlorophenyl | |
| 47 | SC(S)NR'R | CH$_3$ | 2-bromo-4-fluorophenyl | |
| 48 | SC(S)NR'R | CH$_3$ | 3-bromo-4-fluorophenyl | |
| 49 | SC(S)NR'R | CH$_3$ | 3-chloro-4-fluorophenyl | |
| 50 | SC(S)NR'R | CH$_3$ | 3-fluoro-4-chlorophenyl | |
| 51 | SC(S)NR'R | CH$_3$ | 2-cyanophenyl | |
| 52 | SC(S)NR'R | CH$_3$ | 3-cyanophenyl | |
| 53 | SC(S)NR'R | CH$_3$ | 4-cyanophenyl | |
| 54 | SC(S)NR'R | CH$_3$ | 2-nitrophenyl | |
| 55 | SC(S)NR'R | CH$_3$ | 3-nitrophenyl | |
| 56 | SC(S)NR'R | CH$_3$ | 4-nitrophenyl | |
| 57 | SC(S)NR'R | CH$_3$ | 2-methylphenyl | |
| 58 | SC(S)NR'R | CH$_3$ | 3-methylphenyl | |
| 59 | SC(S)NR'R | CH$_3$ | 4-methylphenyl | |
| 60 | SC(S)NR'R | CH$_3$ | 2,4-dimethylphenyl | |
| 61 | SC(S)NR'R | CH$_3$ | 2,6-dimethylphenyl | |
| 62 | SC(S)NR'R | CH$_3$ | 3,4-dimethylphenyl | |
| 63 | SC(S)NR'R | CH$_3$ | 3,5-dimethylphenyl | |

TABLE 3-continued

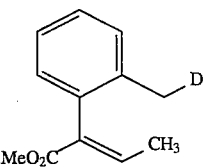

| No. | D | R' | R | phys. data[a] |
|---|---|---|---|---|
| 64 | SC(S)NR'R | CH$_3$ | 2,3,4-trimethylphenyl | |
| 65 | SC(S)NR'R | CH$_3$ | 2,3,5-trimethylphenyl | |
| 66 | SC(S)NR'R | CH$_3$ | 2,3,6-trimethylphenyl | |
| 67 | SC(S)NR'R | CH$_3$ | 2,4,5-trimethylphenyl | |
| 68 | SC(S)NR'R | CH$_3$ | 2,4,6-trimethylphenyl | |
| 69 | SC(S)NR'R | CH$_3$ | 3,4,5-trimethylphenyl | |
| 70 | SC(S)NR'R | CH$_3$ | pentamethylphenyl | |
| 71 | SC(S)NR'R | CH$_3$ | 2-ethylphenyl | |
| 72 | SC(S)NR'R | CH$_3$ | 3-ethylphenyl | |
| 73 | SC(S)NR'R | CH$_3$ | 4-ethylphenyl | |
| 74 | SC(S)NR'R | CH$_3$ | 3,5-diethylphenyl | |
| 75 | SC(S)NR'R | CH$_3$ | 2-n-propylphenyl | |
| 76 | SC(S)NR'R | CH$_3$ | 3-n-propylphenyl | |
| 77 | SC(S)NR'R | CH$_3$ | 4-n-propylphenyl | |
| 78 | SC(S)NR'R | CH$_3$ | 2-isopropylphenyl | |
| 79 | SC(S)NR'R | CH$_3$ | 3-isopropylphenyl | |
| 80 | SC(S)NR'R | CH$_3$ | 4-isopropylphenyl | |
| 81 | SC(S)NR'R | CH$_3$ | 2,4-diisopropylphenyl | |
| 82 | SC(S)NR'R | CH$_3$ | 3,5-diisopropylphenyl | |
| 83 | SC(S)NR'R | CH$_3$ | 4-n-butyphenyl | |
| 84 | SC(S)NR'R | CH$_3$ | 4-sec.-butylphenyl | |
| 85 | SC(S)NR'R | CH$_3$ | 4-iso-butylphenyl | |
| 86 | SC(S)NR'R | CH$_3$ | 4-tert.-butylphenyl | |
| 87 | SC(S)NR'R | CH$_3$ | 3-tert.-butylphenyl | |
| 88 | SC(S)NR'R | CH$_3$ | 2-tert.-butylphenyl | |
| 89 | SC(S)NR'R | CH$_3$ | 2,4-di-tert.-butylphenyl | |
| 90 | SC(S)NR'R | CH$_3$ | 3,5-di-tert.-butylphenyl | |
| 91 | SC(S)NR'R | CH$_3$ | 4-n-hexylphenyl | |
| 92 | SC(S)NR'R | CH$_3$ | 4-n-dodecylphenyl | |
| 93 | SC(S)NR'R | CH$_3$ | 2-methyl-4-tert.-butylphenyl | |
| 94 | SC(S)NR'R | CH$_3$ | 2-methyl-6-tert.-butylphenyl | |
| 95 | SC(S)NR'R | CH$_3$ | 2-methyl-4-isopropylphenyl | |
| 96 | SC(S)NR'R | CH$_3$ | 2-methyl-4-cyclohexylphenyl | |
| 97 | SC(S)NR'R | CH$_3$ | 2-methyl-4-phenylphenyl | |
| 98 | SC(S)NR'R | CH$_3$ | 2-methyl-4-benzylphenyl | |
| 99 | SC(S)NR'R | CH$_3$ | 2-methyl-4-phenoxyphenyl | |
| 100 | SC(S)NR'R | CH$_3$ | 2-methyl-4-benzyloxyphenyl | |
| 101 | SC(S)NR'R | CH$_3$ | 2-methyl-3-chlorophenyl | |
| 102 | SC(S)NR'R | CH$_3$ | 2-methyl-4-chlorophenyl | |
| 103 | SC(S)NR'R | CH$_3$ | 2-methyl-5-chlorophenyl | |
| 104 | SC(S)NR'R | CH$_3$ | 2-methyl-6-chlorophenyl | |
| 105 | SC(S)NR'R | CH$_3$ | 2-methyl-4-fluorophenyl | |
| 106 | SC(S)NR'R | CH$_3$ | 2-methyl-3-bromophenyl | |
| 107 | SC(S)NR'R | CH$_3$ | 2-methyl-4-bromophenyl | |
| 108 | SC(S)NR'R | CH$_3$ | 2-methyl-3-methoxyphenyl | |
| 109 | SC(S)NR'R | CH$_3$ | 2-methyl-4-methoxyphenyl | |
| 110 | SC(S)NR'R | CH$_3$ | 2-methyl-5-methoxyphenyl | |
| 111 | SC(S)NR'R | CH$_3$ | 2-methyl-6-methoxyphenyl | |
| 112 | SC(S)NR'R | CH$_3$ | 2-methyl-4-isopropoxyphenyl | |
| 113 | SC(S)NR'R | CH$_3$ | 2-methyl-2,5-dimethoxyphenyl | |
| 114 | SC(S)NR'R | CH$_3$ | 2-methoxyphenyl | |
| 115 | SC(S)NR'R | CH$_3$ | 3-methoxyphenyl | |
| 116 | SC(S)NR'R | CH$_3$ | 4-methoxyphenyl | |
| 117 | SC(S)NR'R | CH$_3$ | 2,3-dimethoxyphenyl | |
| 118 | SC(S)NR'R | CH$_3$ | 2,4-dimethoxyphenyl | |
| 119 | SC(S)NR'R | CH$_3$ | 2,5-dimethoxyphenyl | |
| 120 | SC(S)NR'R | CH$_3$ | 2,6-dimethoxyphenyl | |

TABLE 3-continued

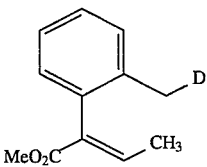

| No. | D | R' | R | phys. data[a] |
|---|---|---|---|---|
| 121 | SC(S)NR'R | CH$_3$ | 3,4-dimethoxyphenyl | |
| 122 | SC(S)NR'R | CH$_3$ | 3,5-dimethoxyphenyl | |
| 123 | SC(S)NR'R | CH$_3$ | 3,6-dimethoxyphenyl | |
| 124 | SC(S)NR'R | CH$_3$ | 2,3,4-trimethoxyphenyl | |
| 125 | SC(S)NR'R | CH$_3$ | 2,3,5-trimethoxyphenyl | |
| 126 | SC(S)NR'R | CH$_3$ | 2,3,6-trimethoxyphenyl | |
| 127 | SC(S)NR'R | CH$_3$ | 2,4,5-trichlorophenyl | |
| 128 | SC(S)NR'R | CH$_3$ | 2,4,6-trichloroyphenyl | |
| 129 | SC(S)NR'R | CH$_3$ | 2,3,4,6-tetrachlorophenyl | |
| 130 | SC(S)NR'R | CH$_3$ | 2,3,5,6-tetrachlorophenyl | |
| 131 | SC(S)NR'R | CH$_3$ | 2-bromophenyl | |
| 132 | SC(S)NR'R | CH$_3$ | 3-bromophenyl | |
| 133 | SC(S)NR'R | CH$_3$ | 4-bromophenyl | |
| 134 | SC(S)NR'R | CH$_3$ | 2,4-dibromophenyl | |
| 135 | SC(S)NR'R | CH$_3$ | 3-bromo-4-fluorophenyl | |
| 136 | SC(S)NR'R | CH$_3$ | 3-bromo-4-methoxyphenyl | |
| 137 | SC(S)NR'R | CH$_3$ | 2-iodophenyl | |
| 138 | SC(S)NR'R | CH$_3$ | 3-iodophenyl | |
| 139 | SC(S)NR'R | CH$_3$ | 4-iodophenyl | |
| 140 | SC(S)NR'R | CH$_3$ | 2-chloro-4-fluorophenyl | |
| 141 | SC(S)NR'R | CH$_3$ | 2-chloro-5-fluorophenyl | |
| 142 | SC(S)NR'R | CH$_3$ | 2-chloro-6-fluorophenyl | |
| 143 | SC(S)NR'R | CH$_3$ | 2-chloro-4-bromophenyl | |
| 144 | SC(S)NR'R | CH$_3$ | 2-bromo-4-chlorophenyl | |
| 145 | SC(S)NR'R | CH$_3$ | 2-bromo-4-fluorophenyl | |
| 146 | SC(S)NR'R | CH$_3$ | 3-bromo-4-chlorophenyl | |
| 147 | SC(S)NR'R | CH$_3$ | 3-chloro-4-fluorophenyl | |
| 148 | SC(S)NR'R | CH$_3$ | 3-fluoro-4-chlorophenyl | |
| 149 | SC(S)NR'R | CH$_3$ | 2-cyanophenyl | |
| 150 | SC(S)NR'R | CH$_3$ | 3-cyanophenyl | |
| 151 | SC(S)NR'R | CH$_3$ | 4-cyanophenyl | |
| 152 | SC(S)NR'R | CH$_3$ | 2-nitrophenyl | |
| 153 | SC(S)NR'R | CH$_3$ | 3-nitrophenyl | |
| 154 | SC(S)NR'R | CH$_3$ | 4-nitrophenyl | |
| 155 | SC(S)NR'R | CH$_3$ | 2-methylphenyl | |
| 156 | SC(S)NR'R | CH$_3$ | 3-methylphenyl | |
| 157 | SC(S)NR'R | CH$_3$ | 4-methylphenyl | |
| 158 | SC(S)NR'R | CH$_3$ | 2,4-dimethylphenyl | |
| 159 | SC(S)NR'R | CH$_3$ | 2,6-dimethylphenyl | |
| 160 | SC(S)NR'R | CH$_3$ | 3,4-dimethylphenyl | |
| 161 | SC(S)NR'R | CH$_3$ | 3,5-dimethylphenyl | |
| 162 | SC(S)NR'R | CH$_3$ | 2,3,4-trimethylphenyl | |
| 163 | SC(S)NR'R | CH$_3$ | 2,3,5-trimethylphenyl | |
| 164 | SC(S)NR'R | CH$_3$ | 2,3,6-trimethylphenyl | |
| 165 | SC(S)NR'R | CH$_3$ | 2,4,5-trimethylphenyl | |
| 166 | SC(S)NR'R | CH$_3$ | 2,4,6-trimethylphenyl | |
| 167 | SC(S)NR'R | CH$_3$ | 2,4,5-trimethylphenyl | |
| 168 | SC(S)NR'R | CH$_3$ | pentamethylphenyl | |
| 169 | SC(S)NR'R | CH$_3$ | 2-ethylphenyl | |
| 170 | SC(S)NR'R | CH$_3$ | 3-ethylphenyl | |
| 171 | SC(S)NR'R | CH$_3$ | 4-ethylphenyl | |
| 172 | SC(S)NR'R | CH$_3$ | 3,5-diethylphenyl | |
| 173 | SC(S)NR'R | CH$_3$ | 2-n-propylphenyl | |
| 174 | SC(S)NR'R | CH$_3$ | 3-n-propylphenyl | |
| 175 | SC(S)NR'R | CH$_3$ | 4-n-propylphenyl | |
| 176 | SC(S)NR'R | CH$_3$ | 2,4,5-trimethoxyphenyl | |
| 177 | SC(S)NR'R | CH$_3$ | 2,4,6-trimethoxyphenyl | |
| 178 | SC(S)NR'R | CH$_3$ | 3,4,5-trimethoxyphenyl | |
| 179 | SC(S)NR'R | CH$_3$ | 2-ethoxyphenyl | |
| 180 | SC(S)NR'R | CH$_3$ | 3-ethoxyphenyl | |
| 181 | SC(S)NR'R | CH$_3$ | 4-ethoxyphenyl | |
| 182 | SC(S)NR'R | CH$_3$ | 2-isopropoxyphenyl | |
| 183 | SC(S)NR'R | CH$_3$ | 3-isopropoxyphenyl | |
| 184 | SC(S)NR'R | CH$_3$ | 4-isopropoxyphenyl | |
| 185 | SC(S)NR'R | CH$_3$ | 3-tert.-butoxyphenyl | |
| 186 | SC(S)NR'R | CH$_3$ | 4-tert.-butoxyphenyl | |
| 187 | SC(S)NR'R | CH$_3$ | 2-trifluoromethoxyphenyl | |

TABLE 3-continued

![structure: 2-substituted styrene with MeO2C and CH3 groups, CH2-D substituent]

| No. | D | R' | R | phys. data[a] |
|---|---|---|---|---|
| 188 | SC(S)NR'R | CH$_3$ | 3-trifluoromethoxyphenyl | |
| 189 | SC(S)NR'R | CH$_3$ | 4-trifluoromethoxyphenyl | |
| 190 | SC(S)NR'R | CH$_3$ | 3-(1',1',2',2'-tetrafluoro)-ethoxyphenyl | |
| 191 | SC(S)NR'R | CH$_3$ | 4-(1',1',2',2'-tetrafluoro)-ethoxyphenyl | |
| 192 | SC(S)NR'R | CH$_3$ | 2-chloromethylphenyl | |
| 193 | SC(S)NR'R | CH$_3$ | 3-chloromethylphenyl | |
| 194 | SC(S)NR'R | CH$_3$ | 4-chloromethylphenyl | |
| 195 | SC(S)NR'R | CH$_3$ | 2-trifluoromethylphenyl | |
| 196 | SC(S)NR'R | CH$_3$ | 3-trifluoromethylphenyl | |
| 197 | SC(S)NR'R | CH$_3$ | 4-trifluoromethylphenyl | |
| 198 | SC(S)NR'R | CH$_3$ | 2-(methoxyiminomethyl)-phenyl | |
| 199 | SC(S)NR'R | CH$_3$ | 3-(methoxyiminomethyl)-phenyl | |
| 200 | SC(S)NR'R | CH$_3$ | 4-(methoxyiminomethyl)-phenyl | |
| 201 | SC(S)NR'R | CH$_3$ | 2-(ethoxyiminomethyl)-phenyl | |
| 202 | SC(S)NR'R | CH$_3$ | 3-(ethoxyiminomethyl)-phenyl | |
| 203 | SC(S)NR'R | CH$_3$ | 4-(ethoxyiminomethyl)-phenyl | |
| 204 | SC(S)NR'R | CH$_3$ | 2-methyl-4-methoximinoethyl-phenyl | |
| 205 | SC(S)NR'R | CH$_3$ | 2-methyl-4-methoximinomethyl-phenyl | |
| 206 | SC(S)NR'R | CH$_3$ | 2,6-dimethyl-4-methoximinomethyl-phenyl | |
| 207 | SC(S)NR'R | CH$_3$ | 2,6-dimethyl-4-methoximinoethyl-phenyl | |
| 208 | SC(S)NR'R | CH$_3$ | 2-phenylphenyl | |
| 209 | SC(S)NR'R | CH$_3$ | 3-phenylphenyl | |
| 210 | SC(S)NR'R | CH$_3$ | 4-phenylphenyl | |
| 211 | SC(S)NR'R | CH$_3$ | 2-phenoxyphenyl | |
| 212 | SC(S)NR'R | CH$_3$ | 3-phenoxyphenyl | |
| 213 | SC(S)NR'R | CH$_3$ | 4-phenoxyphenyl | |
| 214 | SC(S)NR'R | CH$_3$ | 2-benzyloxyphenyl | |
| 215 | SC(S)NR'R | CH$_3$ | 3-benzyloxyphenyl | |
| 216 | SC(S)NR'R | CH$_3$ | 4-benzyloxyphenyl | |
| 217 | SC(S)NR'R | CH$_3$ | 4-(imidazol-1'-yl)phenyl | |
| 218 | SC(S)NR'R | CH$_3$ | 4-(piperazin-1'-yl)phenyl | |
| 219 | SC(S)NR'R | CH$_3$ | 4-(morpholin-1'-yl)-phenyl | |
| 220 | SC(S)NR'R | CH$_3$ | 4-(piperidin-1'-yl)phenyl | |
| 221 | SC(S)NR'R | CH$_3$ | 4-(pyridyl-2'-oxy)phenyl | |
| 222 | SC(S)NR'R | CH$_3$ | 2-cyclopropylphenyl | |
| 223 | SC(S)NR'R | CH$_3$ | 3-cyclopropylphenyl | |
| 224 | SC(S)NR'R | CH$_3$ | 4-cyclopropylphenyl | |
| 225 | SC(S)NR'R | CH$_3$ | 3-cyclohexylphenyl | |
| 226 | SC(S)NR'R | CH$_3$ | 4-cyclohexylphenyl | |
| 227 | SC(S)NR'R | CH$_3$ | 4-oxiranylphenyl | |
| 228 | SC(S)NR'R | CH$_3$ | 4-(1',3'-dioxan-2'-yl)-phenyl | |
| 229 | SC(S)NR'R | CH$_3$ | 4-(tetrahydropyran-2-yl-oxy)-phenyl | |
| 230 | SC(S)NR'R | CH$_3$ | 1-naphthyl | |
| 231 | SC(S)NR'R | CH$_3$ | 2-naphthyl | |
| 232 | SC(S)NR'R | CH$_3$ | benzyl | |
| 233 | SC(S)NR'R | CH$_3$ | 2-methylbenzyl | |
| 234 | SC(S)NR'R | CH$_3$ | 3-methylbenzyl | |
| 235 | SC(S)NR'R | CH$_3$ | 4-methylbenzyl | |
| 236 | SC(S)NR'R | CH$_3$ | 4-tert.-butylbenzyl | |
| 237 | SC(S)NR'R | CH$_3$ | 2-chlorobenzyl | |
| 238 | SC(S)NR'R | CH$_3$ | 3-chlorobenzyl | |
| 239 | SC(S)NR'R | CH$_3$ | 4-chlorobenzyl | |
| 240 | SC(S)NR'R | CH$_3$ | 2-pyridyl | |
| 241 | SC(S)NR'R | CH$_3$ | 3-pyridyl | |
| 242 | SC(S)NR'R | CH$_3$ | 4-pyridyl | |
| 243 | SC(S)NR'R | CH$_3$ | 2,6-pyrimidinyl | |
| 244 | SC(S)NR'R | CH$_3$ | 1,5-pyrimidinyl | |
| 245 | SC(S)NR'R | CH$_3$ | 2-thienyl | |
| 246 | SC(S)NR'R | CH$_3$ | 3-thienyl | |
| 247 | SC(S)NR'R | CH$_3$ | 2-furyl | |
| 248 | SC(S)NR'R | CH$_3$ | 3-furyl | |
| 249 | SC(S)NR'R | CH$_3$ | 1-pyrrolyl | |
| 250 | SC(S)NR'R | CH$_3$ | 1-imidazolyl | |
| 251 | SC(S)NR'R | CH$_3$ | 1,2,4-triazolyl | |
| 252 | SC(S)NR'R | CH$_3$ | 1,3,4-triazolyl | |
| 253 | SC(S)NR'R | CH$_3$ | 4-thiazolyl | |
| 254 | SC(S)NR'R | CH$_3$ | 2-benzothiazolyl | |
| 255 | SC(S)NR'R | CH$_3$ | 2-pyridylmethyl | |
| 256 | SC(S)NR'R | CH$_3$ | 3-pyridylmethyl | |
| 257 | SC(S)NR'R | CH$_3$ | 4-pyridylmethyl | |
| 258 | SC(S)NR'R | Et | phenyl | |
| 259 | SC(S)NR'R | Et | 2-methylphenyl | |
| 260 | SC(S)NR'R | Et | 2-chlorophenyl | |
| 261 | SC(S)NR'R | Et | 4-methylphenyl | |
| 262 | SC(S)NR'R | Et | 2-naphtyl | |
| 263 | SC(S)SR | — | CH$_3$ | |
| 264 | SC(S)SR | — | CH$_2$-phenyl | |
| 265 | SC(S)SR | — | phenyl | |
| 266 | SC(S)SR | — | A* | |
| 267 | SC(S)OR | — | CH$_3$ | |
| 268 | SC(S)OR | — | phenyl | |
| 269 | SC(S)OR | — | 2-CH$_3$-phenyl | |
| 270 | SC(S)OR | — | 3-CH$_3$-phenyl | |
| 271 | SC(S)OR | — | 4-CH$_3$-phenyl | |
| 272 | SC(S)OR | — | 2-Cl-phenyl | |
| 273 | SC(S)OR | — | 3-Cl-phenyl | |
| 274 | SC(S)OR | — | 4-Cl-phenyl | |
| 275 | SC(S)OR | — | CH$_2$-phenyl | |
| 276 | SC(S)OR | — | CH$_2$—(2-Me)-phenyl | |
| 277 | SC(S)OR | — | CH$_2$—(3-Me)-phenyl | |
| 278 | SC(S)OR | — | CH$_2$—(4-Me)-phenyl | |
| 279 | SC(S)OR | — | CH$_2$—(2-Cl)-phenyl | |
| 280 | SC(S)OR | — | CH$_2$—(3-Cl)phenyl | |
| 281 | SC(S)OR | — | CH$_2$—(4-Cl)phenyl | |
| 282 | OC(O)OR | — | CH$_3$ | |
| 283 | OC(O)OR | — | tert.-butyl | |
| 284 | OC(O)OR | — | CH$_2$-phenyl | |
| 285 | OC(O)OR | — | phenyl | |
| 286 | SC(S)NR'R | CH$_3$ | 3-Me, 4-F-phenyl | |

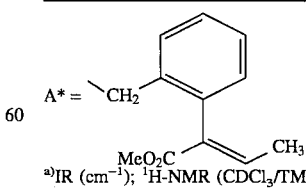

$$A^* = \text{—CH}_2\text{—}$$ (attached to 2-substituted styrene with MeO$_2$C and CH$_3$)

[a] IR (cm$^{-1}$); $^1$H-NMR (CDCl$_3$/TMS); m. p.

TABLE 4

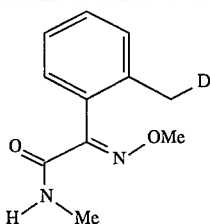

| No. | D | R' | R | phys. data[a] |
|---|---|---|---|---|
| 1 | SC(S)NR'R | CH₃ | methyl | |
| 2 | SC(S)NR'R | CH₃ | ethyl | |
| 3 | SC(S)NR'R | CH₃ | n-propyl | |
| 4 | SC(S)NR'R | CH₃ | tert.-butyl | |
| 5 | SC(S)NR'R | CH₃ | cyclopropyl | |
| 6 | SC(S)NR'R | CH₃ | cyclohexyl | |
| 7 | SC(S)NR'R | CH₃ | methoxymethyl | |
| 8 | SC(S)NR'R | CH₃ | phenoxymethyl | |
| 9 | SC(S)NR'R | CH₃ | methylthiomethyl | |
| 10 | SC(S)NR'R | CH₃ | phenyl | |
| 11 | SC(S)NR'R | CH₃ | 2-fluorophenyl | |
| 12 | SC(S)NR'R | CH₃ | 3-fluorophenyl | |
| 13 | SC(S)NR'R | CH₃ | 4-flourophenyl | 152–156° C. |
| 14 | SC(S)NR'R | CH₃ | pentafluorophenyl | |
| 15 | SC(S)NR'R | CH₃ | 2-chlorophenyl | |
| 16 | SC(S)NR'R | CH₃ | 3-chlorophenyl | 2.90(d, 3H), 3.71, 3.89(2×3H), 4.35 (2H), 6.72(1H), 7.10–7.46(8H) |
| 17 | SC(S)NR'R | CH₃ | 4-chlorophenyl | |
| 18 | SC(S)NR'R | CH₃ | pentachlorophenyl | |
| 19 | SC(S)NR'R | CH₃ | 2,3-dichlorophenyl | |
| 20 | SC(S)NR'R | CH₃ | 2,,4-dichlorophenyl | |
| 21 | SC(S)NR'R | CH₃ | 2,5-dichlorophenyl | |
| 22 | SC(S)NR'R | CH₃ | 2,6-dichlorophenyl | |
| 23 | SC(S)NR'R | CH₃ | 3,4-dichlorophenyl | |
| 24 | SC(S)NR'R | CH₃ | 3,5-dichlorophenyl | |
| 25 | SC(S)NR'R | CH₃ | 2,3,4-trichlorophenyl | |
| 26 | SC(S)NR'R | CH₃ | 2,3,5-trichlorophenyl | |
| 27 | SC(S)NR'R | CH₃ | 2,3,6-trichlorophenyl | |
| 28 | SC(S)NR'R | CH₃ | 2,4,5-trichlorophenyl | |
| 29 | SC(S)NR'R | CH₃ | 2,4,6-trichlorophenyl | |
| 30 | SC(S)NR'R | CH₃ | 3,4,5-trichlorophenyl | |
| 31 | SC(S)NR'R | CH₃ | 2,3,4,6-tetrachlorophenyl | |
| 32 | SC(S)NR'R | CH₃ | 2,3,5,6-tetrachlorophenyl | |
| 33 | SC(S)NR'R | CH₃ | 2-bromophenyl | |
| 34 | SC(S)NR'R | CH₃ | 3-bromophenyl | |
| 35 | SC(S)NR'R | CH₃ | 4-bromophenyl | |
| 36 | SC(S)NR'R | CH₃ | 2,4-dibromophenyl | |
| 37 | SC(S)NR'R | CH₃ | 3-bromo-4-florophenyl | |
| 38 | SC(S)NR'R | CH₃ | 3-bromo-4-methoxyphenyl | |
| 39 | SC(S)NR'R | CH₃ | 2-iodophenyl | |
| 40 | SC(S)NR'R | CH₃ | 3-iodophenyl | |
| 41 | SC(S)NR'R | CH₃ | 4-iodophenyl | |
| 42 | SC(S)NR'R | CH₃ | 2-chloro-4-fluorophenyl | |
| 43 | SC(S)NR'R | CH₃ | 2-chloro-5-fluorophenyl | |
| 44 | SC(S)NR'R | CH₃ | 2-chloro-6-fluorophenyl | |
| 45 | SC(S)NR'R | CH₃ | 2-chloro-4-bromophenyl | |
| 46 | SC(S)NR'R | CH₃ | 2-bromo-4-chlorophenyl | |
| 47 | SC(S)NR'R | CH₃ | 2-bromo-4-flourophenyl | |
| 48 | SC(S)NR'R | CH₃ | 3-bromo-4-fluorophenyl | |
| 49 | SC(S)NR'R | CH₃ | 3-chloro-4-flourophenyl | |
| 50 | SC(S)NR'R | CH₃ | 3-fluoro-4-chlorophenyl | |
| 51 | SC(S)NR'R | CH₃ | 2-cyanophenyl | |
| 52 | SC(S)NR'R | CH₃ | 3-cyanophenyl | |
| 53 | SC(S)NR'R | CH₃ | 4-cyanophenyl | |
| 54 | SC(S)NR'R | CH₃ | 2-nitrophenyl | |
| 55 | SC(S)NR'R | CH₃ | 3-nitrophenyl | |
| 56 | SC(S)NR'R | CH₃ | 4-nitrophenyl | |
| 57 | SC(S)NR'R | CH₃ | 2-methylphenyl | |
| 58 | SC(S)NR'R | CH₃ | 3-methylphenyl | 2.36; 3.74; 3.88(3×3H); 2.90(d, 3H); 4.34(2H); 6.69(1H); 7.02–7.47(8H) |
| 59 | SC(S)NR'R | CH₃ | 4-methylphenyl | 2.35; 3.72; 3.88(3×3H); 2.89(d, 3H); 4.32(2H); 6.67(1H); 7.05–7.43(8H) |
| 60 | SC(S)NR'R | CH₃ | 2,4-dimethylphenyl | |
| 61 | SC(S)NR'R | CH₃ | 2,6-dimethylphenyl | |
| 62 | SC(S)NR'R | CH₃ | 3,4-dimethylphenyl | |
| 63 | SC(S)NR'R | CH₃ | 3,5-dimethylphenyl | |

TABLE 4-continued

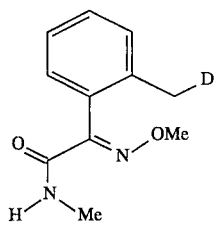

| No. | D | R' | R | phys. data[a)] |
|---|---|---|---|---|
| 64 | SC(S)NR'R | CH₃ | 2,3,4-trimethylphenyl | |
| 65 | SC(S)NR'R | CH₃ | 2,3,5-trimethylphenyl | |
| 66 | SC(S)NR'R | CH₃ | 2,3,6-trimethylphenyl | |
| 67 | SC(S)NR'R | CH₃ | 2,4,5-trimethylphenyl | |
| 68 | SC(S)NR'R | CH₃ | 2,4,6-trimethylphenyl | |
| 69 | SC(S)NR'R | CH₃ | 3,4,5-trimethylphenyl | |
| 70 | SC(S)NR'R | CH₃ | pentamethylphenyl | |
| 71 | SC(S)NR'R | CH₃ | 2-ethylphenyl | |
| 72 | SC(S)NR'R | CH₃ | 3-ethylphenyl | |
| 73 | SC(S)NR'R | CH₃ | 4-ethylphenyl | |
| 74 | SC(S)NR'R | CH₃ | 3,5-diethylphenyl | |
| 75 | SC(S)NR'R | CH₃ | 2-n-propylphenyl | |
| 76 | SC(S)NR'R | CH₃ | 3-n-propylphenyl | |
| 77 | SC(S)NR'R | CH₃ | 4-n-propylphenyl | |
| 78 | SC(S)NR'R | CH₃ | 2-isopropylphenyl | |
| 79 | SC(S)NR'R | CH₃ | 3-isopropylphenyl | |
| 80 | SC(S)NR'R | CH₃ | 4-isopropylphenyl | |
| 81 | SC(S)NR'R | CH₃ | 2,4-diisopropylphenyl | |
| 82 | SC(S)NR'R | CH₃ | 3,5-diisopropylphenyl | |
| 83 | SC(S)NR'R | CH₃ | 4-n-butyphenyl | |
| 84 | SC(S)NR'R | CH₃ | 4-sec.-butylphenyl | |
| 85 | SC(S)NR'R | CH₃ | 4-iso-butylphenyl | |
| 86 | SC(S)NR'R | CH₃ | 4-tert.-butylphenyl | |
| 87 | SC(S)NR'R | CH₃ | 3-tert.-butylphenyl | |
| 88 | SC(S)NR'R | CH₃ | 2-tert.-butylphenyl | |
| 89 | SC(S)NR'R | CH₃ | 2,4-di-tert.-butylphenyl | |
| 90 | SC(S)NR'R | CH₃ | 3,5-di-tert.-butylphenyl | |
| 91 | SC(S)NR'R | CH₃ | 4-n-hexylphenyl | |
| 92 | SC(S)NR'R | CH₃ | 4-n-dodecylphenyl | |
| 93 | SC(S)NR'R | CH₃ | 2-methyl-4-tert.-butylphenyl | |
| 94 | SC(S)NR'R | CH₃ | 2-methyl-6-tert.-butylphenyl | |
| 95 | SC(S)NR'R | CH₃ | 2-methyl-4-isopropylphenyl | |
| 96 | SC(S)NR'R | CH₃ | 2-methyl-4-cyclohexylphenyl | |
| 97 | SC(S)NR'R | CH₃ | 2-methyl-4-phenylphenyl | |
| 98 | SC(S)NR'R | CH₃ | 2-methyl-4-benzylphenyl | |
| 99 | SC(S)NR'R | CH₃ | 2-methyl-4-phenoxyphenyl | |
| 100 | SC(S)NR'R | CH₃ | 2-methyl-4-benzyloxyphenyl | |
| 101 | SC(S)NR'R | CH₃ | 2-methyl-3-chlorophenyl | |
| 102 | SC(S)NR'R | CH₃ | 2-methyl-4-chlorophenyl | |
| 103 | SC(S)NR'R | CH₃ | 2-methyl-5-chlorophenyl | |
| 104 | SC(S)NR'R | CH₃ | 2-methyl-6-chlorophenyl | |
| 105 | SC(S)NR'R | CH₃ | 2-methyl-4-fluorophenyl | |
| 106 | SC(S)NR'R | CH₃ | 2-methyl-3-bromophenyl | |
| 107 | SC(S)NR'R | CH₃ | 2-methyl-4-bromophenyl | |
| 108 | SC(S)NR'R | CH₃ | 2-methyl-3-methoxyphenyl | |
| 109 | SC(S)NR'R | CH₃ | 2-methyl-4-methoxyphenyl | |
| 110 | SC(S)NR'R | CH₃ | 2-methyl-5-methoxyphenyl | |
| 111 | SC(S)NR'R | CH₃ | 2-methyl-6-methoxyphenyl | |
| 112 | SC(S)NR'R | CH₃ | 2-methyl-4-isopropoxyphenyl | |
| 113 | SC(S)NR'R | CH₃ | 2-methyl-2,5-dimethoxyphenyl | |
| 114 | SC(S)NR'R | CH₃ | 2-methoxyphenyl | |
| 115 | SC(S)NR'R | CH₃ | 3-methoxyphenyl | |
| 116 | SC(S)NR'R | CH₃ | 4-methoxyphenyl | |
| 117 | SC(S)NR'R | CH₃ | 2,3-dimethoxyphenyl | |
| 118 | SC(S)NR'R | CH₃ | 2,4-dimethoxyphenyl | |
| 119 | SC(S)NR'R | CH₃ | 2,5-dimethoxyphenyl | |
| 120 | SC(S)NR'R | CH₃ | 2,6-dimethoxyphenyl | |
| 121 | SC(S)NR'R | CH₃ | 3,4-dimethoxyphenyl | |
| 122 | SC(S)NR'R | CH₃ | 3,5-dimethoxyphenyl | |
| 123 | SC(S)NR'R | CH₃ | 3,6-dimethoxyphenyl | |
| 124 | SC(S)NR'R | CH₃ | 2,3,4-trimethoxyphenyl | |
| 125 | SC(S)NR'R | CH₃ | 2,3,5-trimethoxyphenyl | |
| 126 | SC(S)NR'R | CH₃ | 2,3,6-trimethoxyphenyl | |
| 127 | SC(S)NR'R | CH₃ | 2,4,5-trichlorophenyl | |
| 128 | SC(S)NR'R | CH₃ | 2,4,6-trichloroyphenyl | |
| 129 | SC(S)NR'R | CH₃ | 2,3,4,6-tetrachlorophenyl | |

TABLE 4-continued

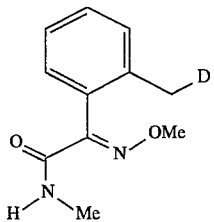

| No. | D | R' | R | phys. data[a] |
|---|---|---|---|---|
| 130 | SC(S)NR'R | CH₃ | 2,3,5,6-tetrachlorophenyl | |
| 131 | SC(S)NR'R | CH₃ | 2-bromophenyl | |
| 132 | SC(S)NR'R | CH₃ | 3-bromophenyl | |
| 133 | SC(S)NR'R | CH₃ | 4-bromophenyl | |
| 134 | SC(S)NR'R | CH₃ | 2,4-dibromophenyl | |
| 135 | SC(S)NR'R | CH₃ | 3-bromo-4-fluorophenyl | |
| 136 | SC(S)NR'R | CH₃ | 3-bromo-4-methoxyphenyl | |
| 137 | SC(S)NR'R | CH₃ | 2-iodophenyl | |
| 138 | SC(S)NR'R | CH₃ | 3-iodophenyl | |
| 139 | SC(S)NR'R | CH₃ | 4-iodophenyl | |
| 140 | SC(S)NR'R | CH₃ | 2-chloro-4-fluorophenyl | |
| 141 | SC(S)NR'R | CH₃ | 2-chloro-5-fluorophenyl | |
| 142 | SC(S)NR'R | CH₃ | 2-chloro-6-fluorophenyl | |
| 143 | SC(S)NR'R | CH₃ | 2-chloro-4-bromophenyl | |
| 144 | SC(S)NR'R | CH₃ | 2-bromo-4-chlorophenyl | |
| 145 | SC(S)NR'R | CH₃ | 2-bromo-4-fluorophenyl | |
| 146 | SC(S)NR'R | CH₃ | 3-bromo-4-chlorophenyl | |
| 147 | SC(S)NR'R | CH₃ | 3-chloro-4-fluorophenyl | |
| 148 | SC(S)NR'R | CH₃ | 3-fluoro-4-chlorophenyl | |
| 149 | SC(S)NR'R | CH₃ | 2-cyanophenyl | |
| 150 | SC(S)NR'R | CH₃ | 3-cyanophenyl | |
| 151 | SC(S)NR'R | CH₃ | 4-cyanophenyl | |
| 152 | SC(S)NR'R | CH₃ | 2-nitrophenyl | |
| 153 | SC(S)NR'R | CH₃ | 3-nitrophenyl | |
| 154 | SC(S)NR'R | CH₃ | 4-nitrophenyl | |
| 155 | SC(S)NR'R | CH₃ | 2-methylphenyl | |
| 156 | SC(S)NR'R | CH₃ | 3-methylphenyl | |
| 157 | SC(S)NR'R | CH₃ | 4-methylphenyl | |
| 158 | SC(S)NR'R | CH₃ | 2,4-dimethylphenyl | |
| 159 | SC(S)NR'R | CH₃ | 2,6-dimethylphenyl | |
| 160 | SC(S)NR'R | CH₃ | 3,4-dimethylphenyl | |
| 161 | SC(S)NR'R | CH₃ | 3,5-dimethylphenyl | |
| 162 | SC(S)NR'R | CH₃ | 2,3,4-trimethylphenyl | |
| 163 | SC(S)NR'R | CH₃ | 2,3,5-trimethylphenyl | |
| 164 | SC(S)NR'R | CH₃ | 2,3,6-trimethylphenyl | |
| 165 | SC(S)NR'R | CH₃ | 2,4,5-trimethylphenyl | |
| 166 | SC(S)NR'R | CH₃ | 2,4,6-trimethylphenyl | |
| 167 | SC(S)NR'R | CH₃ | 2,4,5-trimethylphenyl | |
| 168 | SC(S)NR'R | CH₃ | pentamethylphenyl | |
| 169 | SC(S)NR'R | CH₃ | 2-ethylphenyl | |
| 170 | SC(S)NR'R | CH₃ | 3-ethylphenyl | |
| 171 | SC(S)NR'R | CH₃ | 4-ethylphenyl | |
| 172 | SC(S)NR'R | CH₃ | 3,5-diethylphenyl | |
| 173 | SC(S)NR'R | CH₃ | 2-n-propylphenyl | |
| 174 | SC(S)NR'R | CH₃ | 3-n-propylphenyl | |
| 175 | SC(S)NR'R | CH₃ | 4-n-propylphenyl | |
| 176 | SC(S)NR'R | CH₃ | 2,4,5-trimethoxyphenyl | |
| 177 | SC(S)NR'R | CH₃ | 2,4,6-trimethoxyphenyl | |
| 178 | SC(S)NR'R | CH₃ | 3,4,5-trimethoxyphenyl | |
| 179 | SC(S)NR'R | CH₃ | 2-ethoxyphenyl | |
| 180 | SC(S)NR'R | CH₃ | 3-ethoxyphenyl | |
| 181 | SC(S)NR'R | CH₃ | 4-ethoxyphenyl | |
| 182 | SC(S)NR'R | CH₃ | 2-isopropoxyphenyl | |
| 183 | SC(S)NR'R | CH₃ | 3-isopropoxyphenyl | |
| 184 | SC(S)NR'R | CH₃ | 4-isopropoxyphenyl | |
| 185 | SC(S)NR'R | CH₃ | 3-tert.-butoxyphenyl | |
| 186 | SC(S)NR'R | CH₃ | 4-tert.-butoxyphenyl | |
| 187 | SC(S)NR'R | CH₃ | 2-trifluoromethoxyphenyl | |
| 188 | SC(S)NR'R | CH₃ | 3-trifluoromethoxyphenyl | |
| 189 | SC(S)NR'R | CH₃ | 4-trifluoromethoxyphenyl | |
| 190 | SC(S)NR'R | CH₃ | 3-(1',1',2',2'-tetrafluoro)-ethoxyphenyl | |
| 191 | SC(S)NR'R | CH₃ | 4-(1',1',2',2'-tetrafluoro)-ethoxyphenyl | |
| 192 | SC(S)NR'R | CH₃ | 2-chloromethylphenyl | |
| 193 | SC(S)NR'R | CH₃ | 3-chloromethylphenyl | |
| 194 | SC(S)NR'R | CH₃ | 4-chloromethylphenyl | |
| 195 | SC(S)NR'R | CH₃ | 2-trifluoromethylphenyl | |

TABLE 4-continued

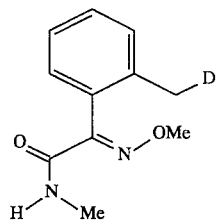

| No. | D | R' | R | phys. data[a] |
|---|---|---|---|---|
| 196 | SC(S)NR'R | CH₃ | 3-trifluoromethylphenyl | |
| 197 | SC(S)NR'R | CH₃ | 4-trifluoromethylphenyl | |
| 198 | SC(S)NR'R | CH₃ | 2-(methoxyiminomethyl)-phenyl | |
| 199 | SC(S)NR'R | CH₃ | 3-(methoxyiminomethyl)-phenyl | |
| 200 | SC(S)NR'R | CH₃ | 4-(methoxyiminomethyl)-phenyl | |
| 201 | SC(S)NR'R | CH₃ | 2-(ethoxyiminomethyl)-phenyl | |
| 202 | SC(S)NR'R | CH₃ | 3-(ethoxyiminomethyl)-phenyl | |
| 203 | SC(S)NR'R | CH₃ | 4-(ethoxyiminomethyl)-phenyl | |
| 204 | SC(S)NR'R | CH₃ | 2-methyl-4-methoximinoethyl-phenyl | |
| 205 | SC(S)NR'R | CH₃ | 2-methyl-4-methoximinomethyl-phenyl | |
| 206 | SC(S)NR'R | CH₃ | 2,6-dimethyl-4-methoximinomethyl-phenyl | |
| 207 | SC(S)NR'R | CH₃ | 2,6-dimethyl-4-methoximinoethyl-phenyl | |
| 208 | SC(S)NR'R | CH₃ | 2-phenylphenyl | |
| 209 | SC(S)NR'R | CH₃ | 3-phenylphenyl | |
| 210 | SC(S)NR'R | CH₃ | 4-phenylphenyl | |
| 211 | SC(S)NR'R | CH₃ | 2-phenoxyphenyl | |
| 212 | SC(S)NR'R | CH₃ | 3-phenoxyphenyl | |
| 213 | SC(S)NR'R | CH₃ | 4-phenyoxphenyl | |
| 214 | SC(S)NR'R | CH₃ | 2-benzyloxyphenyl | |
| 215 | SC(S)NR'R | CH₃ | 3-benzyloxyphenyl | |
| 216 | SC(S)NR'R | CH₃ | 4-benzyloxyphenyl | |
| 217 | SC(S)NR'R | CH₃ | 4-(imidazol-1'-yl)phenyl | |
| 218 | SC(S)NR'R | CH₃ | 4-(piperazin-1'-yl)phenyl | |
| 219 | SC(S)NR'R | CH₃ | 4-(morpholin-1'-yl)phenyl | |
| 220 | SC(S)NR'R | CH₃ | 4-(piperidin-1'-yl)phenyl | |
| 221 | SC(S)NR'R | CH₃ | 4-(pyridyl-2'-oxy)phenyl | |
| 222 | SC(S)NR'R | CH₃ | 2-cyclopropylphenyl | |
| 223 | SC(S)NR'R | CH₃ | 3-cyclopropylphenyl | |
| 224 | SC(S)NR'R | CH₃ | 4-cyclopropylphenyl | |
| 225 | SC(S)NR'R | CH₃ | 3-cyclohexylphenyl | |
| 226 | SC(S)NR'R | CH₃ | 4-cyclohexylphenyl | |
| 227 | SC(S)NR'R | CH₃ | 4-oxiranylphenyl | |
| 228 | SC(S)NR'R | CH₃ | 4-(1',3'-dioxan-2'-yl)-phenyl | |
| 229 | SC(S)NR'R | CH₃ | 4-(tetrahydropyran-2-yl-oxy)-phenyl | |
| 230 | SC(S)NR'R | CH₃ | 1-naphthyl | |
| 231 | SC(S)NR'R | CH₃ | 2-naphthyl | |
| 232 | SC(S)NR'R | CH₃ | benzyl | |
| 233 | SC(S)NR'R | CH₃ | 2-methylbenzyl | |
| 234 | SC(S)NR'R | CH₃ | 3-methylbenzyl | |
| 235 | SC(S)NR'R | CH₃ | 4-methylbenzyl | |
| 236 | SC(S)NR'R | CH₃ | 4-tert.-butylbenzyl | |
| 237 | SC(S)NR'R | CH₃ | 2-chlorobenzyl | |
| 238 | SC(S)NR'R | CH₃ | 3-chlorobenzyl | |
| 239 | SC(S)NR'R | CH₃ | 4-chlorobenzyl | |
| 240 | SC(S)NR'R | CH₃ | 2-pyridyl | |
| 241 | SC(S)NR'R | CH₃ | 3-pyridyl | |
| 242 | SC(S)NR'R | CH₃ | 4-pyridyl | |
| 243 | SC(S)NR'R | CH₃ | 2,6-pyrimidinyl | |
| 244 | SC(S)NR'R | CH₃ | 1,5-pyrimidinyl | |
| 245 | SC(S)NR'R | CH₃ | 2-thienyl | |
| 246 | SC(S)NR'R | CH₃ | 3-thienyl | |
| 247 | SC(S)NR'R | CH₃ | 2-furyl | |
| 248 | SC(S)NR'R | CH₃ | 3-furyl | |
| 249 | SC(S)NR'R | CH₃ | 1-pyrrolyl | |
| 250 | SC(S)NR'R | CH₃ | 1-imidazolyl | |
| 251 | SC(S)NR'R | CH₃ | 1,2,4-triazolyl | |
| 252 | SC(S)NR'R | CH₃ | 1,3,4-triazolyl | |
| 253 | SC(S)NR'R | CH₃ | 4-thiazolyl | |
| 254 | SC(S)NR'R | CH₃ | 2-benzothiazolyl | |
| 255 | SC(S)NR'R | CH₃ | 2-pyridylmethyl | |
| 256 | SC(S)NR'R | CH₃ | 3-pyridylmethyl | |
| 257 | SC(S)NR'R | CH₃ | 4-pyridylmethyl | |
| 258 | SC(S)NR'R | Et | phenyl | 162° C. |
| 259 | SC(S)NR'R | Et | 2-methylphenyl | |
| 260 | SC(S)NR'R | Et | 2-chlorophenyl | |

TABLE 4-continued

[Structure: 2-substituted phenyl compound with CH₂-D group, C(=NOMe), C(=O)NHMe]

| No. | D | R' | R | phys. data[a] |
|---|---|---|---|---|
| 261 | SC(S)NR'R | Et | 4-methylphenyl | 1663, 1523, 1508, 1444, 1399, 1385, 1272, 1103, 1038 |
| 262 | SC(S)NR'R | Et | 2-naphthyl | |
| 263 | SC(S)SR | — | CH₃ | |
| 264 | SC(S)SR | — | CH₂-phenyl | |
| 265 | SC(S)SR | — | phenyl | |
| 266 | SC(S)SR | — | A* | |
| 267 | SC(S)OR | — | CH₃ | |
| 268 | SC(S)OR | — | phenyl | |
| 269 | SC(S)OR | — | 2-CH₃-phenyl | |
| 270 | SC(S)OR | — | 3-CH₃-phenyl | |
| 271 | SC(S)OR | — | 4-CH₃-phenyl | |
| 272 | SC(S)OR | — | 2-Cl-phenyl | |
| 273 | SC(S)OR | — | 3-Cl-phenyl | |
| 274 | SC(S)OR | — | 4-Cl-phenyl | |
| 275 | SC(S)OR | — | CH₂-phenyl | |
| 276 | SC(S)OR | — | CH₂—(2-Me)-phenyl | |
| 277 | SC(S)OR | — | CH₂—(3-Me)-phenyl | |
| 278 | SC(S)OR | — | CH₂—(4-Me)-phenyl | |
| 279 | SC(S)OR | — | CH₂—(2-Cl)-phenyl | |
| 280 | SC(S)OR | — | CH₂—(3-Cl)phenyl | |
| 281 | SC(S)OR | — | CH₂—(4-Cl)phenyl | |
| 282 | OC(O)OR | — | CH₃ | |
| 283 | OC(O)OR | — | tert.-butyl | |
| 284 | OC(O)OR | — | CH₂-phenyl | |
| 285 | OC(O)OR | — | phenyl | 5.13 ppm (CH₂) |
| 286 | SC(S)NR'R | CH₃ | 3-Me, 4-F-phenyl | 2.29; 3.73; 3.90(3×3H), 2.92(d, 3H), 4.35 2H), 6.70(1H), 6.98–7.46(7H) |
| 287 | OC(O)NR'R | H | i-propyl | 138–140° C. |
| 288 | OC(O)NR'R | H | tert.-butyl | 143–145° C. |
| 289 | OC(O)NR'R | H | C(Me)₂C≡C—H | 117–119° C. |
| 290 | OC(O)NR'R | H | 2-Me-phenyl | 140–141° C. |
| 291 | OC(O)NR'R | H | 3-Me-phenyl | 150–152° C. |
| 292 | OC(O)NR'R | H | 4-Me-phenyl | 204–205° C. |
| 293 | OC(O)NR'R | H | 4-F-phenyl | 136–139° C. |
| 294 | OC(O)NR'R | H | 2,6-Cl₂-phenyl | 195–198° C. |
| 295 | OC(O)NR'R | H | 3,5-Cl₂-phenyl | 162–164° C. |

A* = 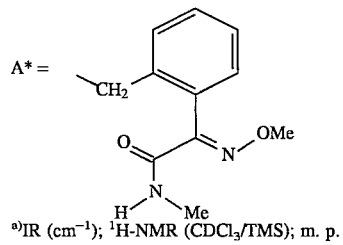

[a] IR (cm⁻¹); ¹H-NMR (CDCl₃/TMS); m. p.

The novel compounds are suitable as fungicides.

The fungicidal compounds, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of such formulations are given below.

I. A solution of 90 parts by weight of compound no. 16 from Table 4 and 10 parts by weight of N-methyl-α-pyrrolidone, which is suitable for application in the form of very fine drops.

II. A mixture of 20 parts by weight of compound no. 58 from Table 4, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 59 from Table 4, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 157 from Table 4, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 286 from Table 4, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor is obtained.

VI. An intimate mixture of 3 parts by weight of compound no. 16 from Table 4 and 97 parts by weight of particulate kaolin. The dust contains 3wt % of the active ingredient.

VII. An intimate mixture of 30 parts by weight of compound no. 58 from Table 4, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 59 from Table 4, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 157 from Table 4, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a remarkably high systemic mobility and action after application to the soil and particularly to foliage.

The fungicidal con, pounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the seeds, plants, materials or soil to be protected against fungus attack with a fungicidally effective amount of the active ingredients.

The compounds may be applied before or after infection of the materials, plants or seeds by the fungi.

The compounds I are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaegualis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), for example against *Paecilomyces variotii*.

The fungicidal agents generally contain from 0.1 to 95, and preferably from 0.5 to 90, wt % of active ingredient.

The application rates depend on the type of effect desired, but are generally from 0.02 to 3 kg of active ingredient per hectare.

When the active ingredients are used for treating seed, application rates of from 0.001 to 50, and preferably from 0.01 to 10, g per kg of seed are generally required.

When the agents according to the invention are used as fungicides, they may be employed together with other active ingredients, e.g., herbicides, insecticides, growth regulators, other fungicides and fertilizers.

When admixed with other fungicides, the spectrum of fungicidal action is in many instances increased.

USE EXAMPLES

The active ingredients used for comparison purposes were methyl α-[2-(phenylthiomethyl)-phenyl]-β-methoxyacrylate (A) and methyl 2-(phenylthiomethyl)-α-methoxyiminophenylacetate (B).

USE EXAMPLE 1

Action on wheat mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. tritici). The plants were then set up in the greenhouse at from 20° to 22° C. and a relative humidity of from 75 to 80%. The extent of mildew spread was assessed after 7 days.

The results show that active ingredient no. 16 from Table 1 has, when applied as a spray liquor containing 63 ppm of active ingredient, a better fungicidal action (15% leaf attack) than prior art comparative agent A (40% leaf attack).

USE EXAMPLE 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were-set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredient no. 13 from Table 2 has, when applied as a spray liquor containing 63 ppm of active ingredient, a better fungicidal action (15% leaf attack) than prior art active ingredient B (40% leaf attack).

We claim:

1. A benzyl compound of the formula I where
A is CH—$C_1$–$C_4$-alkyl,
B is OH, $C_1$–$C_4$-alkylthio, $C_1$–$C_4$-alkoxy or $C_1$–$C_4$-alkylamino,
U, V and W are identical or different and are each hydrogen, halogen, $C_1$–$C_4$-alkyl or $C_1$–$C_4$-alkoxy,
D is where
R' is hydrogen or $C_1$–$C_4$-alkyl and
R is hydrogen, $C_1$–$C_{10}$-alkyl, $C_3$–$C_6$-cycloalkyl, $C_1$–$C_4$-haloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, unsubstituted or substituted arylthio-$C_1$–$C_4$-alkyl, unsubstituted or substituted aryloxy-$C_1$–$C_4$-alkyl, unsubstituted or substituted aryl, unsubstituted or substituted aryl-$C_1$–$C_4$-alkyl, unsubstituted or substituted hetaryl, unsubstituted or substituted hetaryl-$C_1$–$C_4$-alkyl, unsubstituted or substituted hetaryloxy-$C_1$–$C_4$-alkyl or unsubstituted or substituted heterocyclyl, substituents being halogen, cyano, $CO_2$($C_1$–$C_4$-alkyl), CO($C_1$–$C_4$-alkyl), nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy.

2. A benzyl compound of the formula I as claimed in claim 1, wherein A is CH-methyl, B is methoxy and U, V, W and D have the meanings stated in claim 1.

3. A fungicide containing an inert carrier and a fungicidal amount of a benzyl compound of the formula where
A is CH—$C_1$–$C_4$-alkyl,
B is ON, $C_1$–$C_4$-alkylthio, $C_1$–$C_4$-alkoxy or $C_1$–$C_4$-alkylamino,
U, V and W are identical or different and are each hydrogen, halogen, $C_1$–$C_4$-alkyl or $C_1$–$C_4$-alkoxy,
D is where
R' is hydrogen or $C_1$–$C_4$-alkyl and R is hydrogen, $C_1$–$C_{10}$-alkyl, $C_3$–$C_6$-cycloalkyl, $C_1$–$C_4$-haloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, unsubstituted or substituted arylthio-$C_1$–$C_4$-alkyl, unsubstituted or substituted aryloxy-$C_1$–$C_4$-alkyl, unsubstituted or substituted aryl, unsubstituted or substituted aryl-$C_1$–$C_4$-alkyl, unsubstituted or substituted hetaryl, unsubstituted or substituted hetaryl-$C_1$–$C_4$-alkyl, unsubstituted or substituted hetaryloxy-$C_1$–$C_4$-alkyl or unsubstituted or substituted heterocyclyl, substituents being halogen, cyano, $CO_2(C_1$–$C_4$-alkyl), $CO(C_1$–$C_4$-alkyl), nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy.

4. A method for controlling fungi, wherein the fungi or the materials, plants or seed threatened by fungal attack or the soil is or are treated with a fungicidal amount of a compound of the formula I

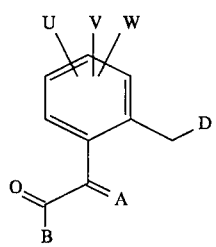

where
A is CH—$C_1$–$C_4$-alkyl,
B is OH, $C_1$–$C_4$-alkylthio, $C_1$–$C_4$-alkoxy or $C_1$–$C_4$-alkylamino,
U, V and W are identical or different and are each hydrogen, halogen, $C_1$–$C_4$-alkyl or $C_1$–$C_4$-alkoxy,
D is

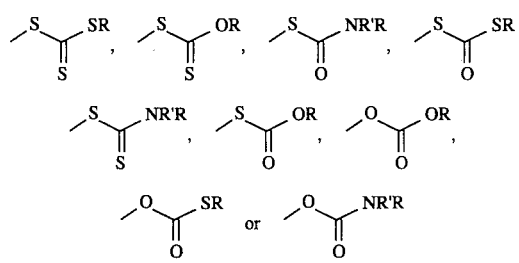

where
R' is hydrogen or $C_1$–$C_4$-alkyl and
R is hydrogen, $C_1$–$C_{10}$-alkyl, $C_3$–$C_6$-cycloalkyl, $C_1$–$C_4$-haloalkyl, $C_3$–$C_6$-halocycloalkyl, $C_3$–$C_6$-cycloalkyl-$C_1$–$C_4$-alkyl, $C_1$–$C_4$-alkoxy-$C_1$–$C_4$-alkyl, $C_1$–$C_4$-alkylthio-$C_1$–$C_4$-alkyl, unsubstituted or substituted arylthio-$C_1$–$C_4$-alkyl, unsubstituted or substituted aryloxy-$C_1$–$C_4$-alkyl, unsubstituted or substituted aryl, unsubstituted or substituted aryl-$C_1$–$C_4$-alkyl, unsubstituted or substituted hetaryl, unsubstituted or substituted hetaryl-$C_1$–$C_4$-alkyl, unsubstituted or substituted hetaryloxy-$C_1$–$C_4$-alkyl or unsubstituted or substituted heterocyclyl, substituents being halogen, cyano, $CO_2(C_1$–$C_4$-alkyl), $CO(C_1$–$C_4$-alkyl), nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy.

5. A method for controlling insects, wherein the insects or the place where the insects are present is or are treated with an insecticidal amount of a compound of the formula I

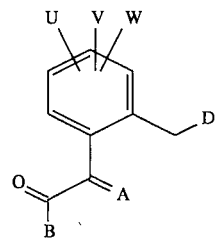

where
A is $CH_2$, or CH—$C_1$–$C_4$-alkyl,
B is OH, $C_1$–$C_4$-alkylthio, $C_1$–$C_4$-alkoxy or $C_1$–$C_4$-alkylamino,
U, V and W are identical or different and are each hydrogen, halogen, $C_1$–$C_4$-alkyl or $C_1$–$C_4$-alkoxy,
D is

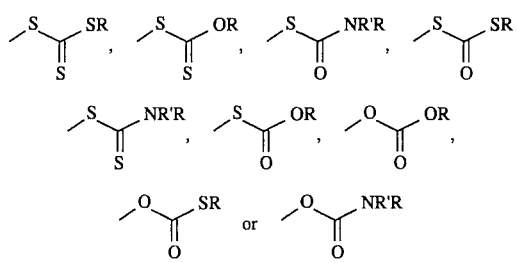

where
R' is hydrogen or $C_1$–$C_4$-alkyl and
R is hydrogen, $C_1$–$C_{10}$-alkyl, $C_3$–$C_6$-cycloalkyl, $C_1$–$C_4$-haloalkyl, $C_3$–$C_6$-halocycloalkyl, $C_3$–$C_6$-cycloalkyl-$C_1$–$C_6$-alkyl, $C_1$–$C_4$-alkoxy-$C_1$–$C_4$-alkyl, $C_1$–$C_4$-alkylthio-$C_1$–$C_4$-alkyl, unsubstituted or substituted arylthio-$C_1$–$C_4$-alkyl, unsubstituted or substituted aryloxy-$C_1$–$C_4$-alkyl, unsubstituted or substituted aryl, unsubstituted or substituted aryl-$C_1$–$C_4$-alkyl, unsubstituted or substituted hetaryl, unsubstituted or substituted hetaryl-$C_1$–$C_4$-alkyl, unsubstituted or substituted hetaryloxy-$C_1$–$C_4$-alkyl or unsubstituted or substituted heterocyclyl, substituents being halogen, cyano, $CO_2(C_1$–$C_4$-alkyl), $CO(C_1$–$C_4$-alkyl), nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$- or $C_2$-alkyl, aryl, aryloxy, benzyloxy, hetaryl, hetaryloxy, $C_3$–$C_6$-cycloalkyl, heterocyclyl or heterocyclyloxy.

6. A benzyl compound of the formula I as claimed in claim 1, wherein D is

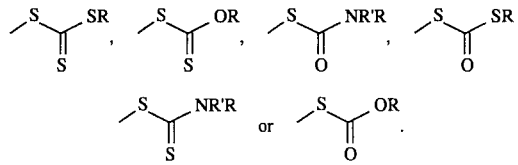

7. A benzyl compound of the formula I as claimed in claim 1, wherein D is

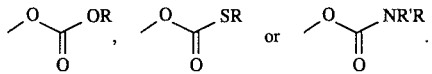

8. A fungicide as claimed in claim 3, wherein D is
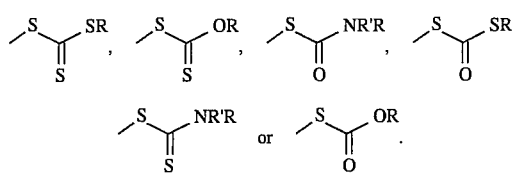
9. A fungicide as claimed in claim 3, wherein D is
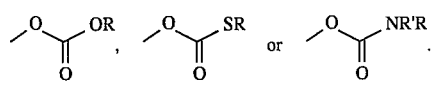
10. A method for controlling fungi as claimed in claim 4, wherein D is
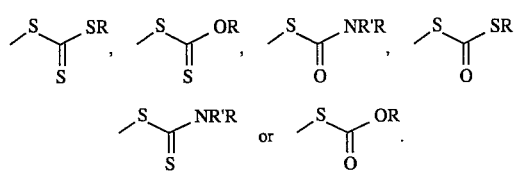
11. A method for controlling fungi as claimed in claim 4, wherein D is
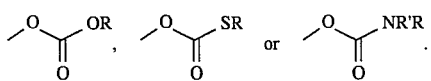
12. A method for controlling insects as claimed in claim 5, wherein D is
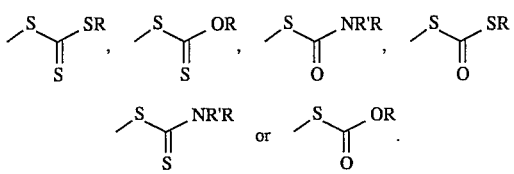
13. A method for controlling insects as claimed in claim 5, wherein D is
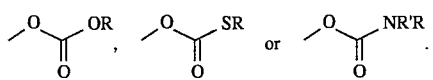
* * * * *